US011266377B2

(12) United States Patent
Ohishi et al.

(10) Patent No.: US 11,266,377 B2
(45) Date of Patent: Mar. 8, 2022

(54) SUPPORT APPARATUS AND SUPPORT METHOD

(71) Applicant: Toshiba Medical Systems Corporation, Otawara (JP)

(72) Inventors: Satoru Ohishi, Otawara (JP); Takayuki Kuwahara, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 453 days.

(21) Appl. No.: 15/588,978

(22) Filed: May 8, 2017

(65) Prior Publication Data
US 2017/0333002 A1 Nov. 23, 2017

(30) Foreign Application Priority Data

May 17, 2016 (JP) .............................. JP2016-098639
Feb. 24, 2017 (JP) .............................. JP2017-033635

(51) Int. Cl.
*A61B 8/00* (2006.01)
*A61N 5/10* (2006.01)
(Continued)

(52) U.S. Cl.
CPC ............ *A61B 8/4263* (2013.01); *A61B 6/032* (2013.01); *A61B 8/085* (2013.01); *A61B 8/4245* (2013.01);
(Continued)

(58) Field of Classification Search
CPC ....... A61B 6/032; A61B 8/085; A61B 8/4263; A61B 8/483; A61B 8/488; A61N 5/103; A61N 5/1049; A61N 2005/1058
See application file for complete search history.

(56) References Cited

U.S. PATENT DOCUMENTS

2009/0003528 A1* 1/2009 Ramraj ................ A61B 6/0457
378/119
2009/0024030 A1* 1/2009 Lachaine ............. A61B 8/4416
600/437
(Continued)

FOREIGN PATENT DOCUMENTS

JP 2007-312860 A 1/2007
JP 2011-072522 A 4/2011
(Continued)

OTHER PUBLICATIONS

McIlwain et al., Radiation Safety for the Cardiac Sonographer: Recommendations of the Radiation Safety Writing Group for the Council on Cardiovascular Sonography of the American Society of Echocardiography, J Am Soc Echocardiogr 2014;27:811-6 (Year: 2014).*

(Continued)

*Primary Examiner* — Amelie R Davis
*Assistant Examiner* — John Denny Li
(74) *Attorney, Agent, or Firm* — Oblon, McClelland, Maier & Neustadt, L.L.P.

(57) ABSTRACT

A support apparatus comprises processing circuitry. The processing circuitry is configured to calculate, based on an irradiation plan with radiation on a target site of a subject, a recommendation degree of disposition of an ultrasonic probe configured to scan the target site at irradiation with the radiation, for each position in the subject. And the processing circuitry is configured to notify an operator of the recommendation degree in association with a position in the subject.

19 Claims, 10 Drawing Sheets

(51) Int. Cl.
*A61B 6/03* (2006.01)
*A61B 8/08* (2006.01)

(52) U.S. Cl.
CPC ............ *A61N 5/103* (2013.01); *A61N 5/1049* (2013.01); *A61B 8/483* (2013.01); *A61B 8/488* (2013.01); *A61N 2005/1058* (2013.01)

(56) References Cited

U.S. PATENT DOCUMENTS

| | | | |
|---|---|---|---|
| 2011/0009742 A1* | 1/2011 | Lachaine | A61B 8/4227 |
| | | | 600/427 |
| 2013/0211243 A1* | 8/2013 | Zhang | A61B 10/0233 |
| | | | 600/424 |
| 2014/0094700 A1* | 4/2014 | Watanabe | G10K 11/346 |
| | | | 600/437 |
| 2014/0344742 A1 | 11/2014 | Wiemker et al. | |
| 2015/0193931 A1 | 7/2015 | Fuchigami et al. | |
| 2015/0209599 A1* | 7/2015 | Schlosser | A61N 5/1049 |
| | | | 600/427 |
| 2015/0294454 A1 | 10/2015 | Nempont et al. | |
| 2016/0030131 A1* | 2/2016 | Yang | A61B 5/055 |
| | | | 600/424 |
| 2017/0333145 A1* | 11/2017 | Griffiths | A61B 34/30 |

FOREIGN PATENT DOCUMENTS

| | | |
|---|---|---|
| JP | 2012-230232 A | 11/2012 |
| JP | 2014-501143 | 1/2014 |
| JP | 2014-61061 | 4/2014 |
| JP | 2015-504690 | 2/2015 |
| JP | 2015-533329 | 11/2015 |
| WO | WO 2012-002420 A1 | 1/2012 |
| WO | WO 2012/088535 A1 | 6/2012 |

OTHER PUBLICATIONS

Pheiffer et al., Model-Based Correction of Tissue Compression for Tracked Ultrasound in Soft Tissue Image-Guided Surgery, Ultrasound Med Biol. Apr. 2014; 40(4): 788-803. Published online Jan. 10, 2014. doi: 10.1016/j.ultrasmedbio.2013.11.003 (Year: 2014).*
Office Action dated Sep. 15, 2020 in corresponding Japanese Patent Application No. 2017-033635.

* cited by examiner

SUPPORT APPARATUS AND SUPPORT METHOD

CROSS-REFERENCE TO RELATED APPLICATIONS

This application is based upon and claims the benefit of priority from Japanese Patent Application No. 2016-098639, filed on May 17, 2017; and Japanese Patent Application No. 2017-033635, filed on Feb. 24, 2017, the entire contents of all of which are incorporated herein by reference.

FIELD

Embodiments described herein relate generally to a support apparatus and a support method.

BACKGROUND

A known conventionally radiation treatment system performs treatment on a target site (for example, a tumor) inside a subject by irradiating the target site with radiation such as X-ray, and has a guide function using an ultrasonic image. For example, the radiation treatment system acquires ultrasonic images of the subject in real time, and irradiates a target site in the subject with radiation when the target site reaches an irradiation position, while checking the position and motion of the target site.

The position of an ultrasonic probe disposed on the subject to acquire ultrasonic images of the target site is determined on the basis of experience of an operator such as a doctor. For example, when determining the position of the ultrasonic probe on the subject on the basis of the experience thereof, the operator considers, for example, degradation of the efficiency of the radiation treatment and degradation of the ultrasonic probe due to radiation incident on the ultrasonic probe, and the image quality of an ultrasonic image to be obtained.

DETAILED DESCRIPTION

A support apparatus comprises processing circuitry. The processing circuitry is configured to calculate, based on an irradiation plan with radiation on a target site of a subject, a recommendation degree of disposition of an ultrasonic probe configured to scan the target site at irradiation with the radiation, for each position in the subject. And the processing circuitry is configured to notify an operator of the recommendation degree in association with a position in the subject.

Embodiments of a support apparatus according to the present application will be described below with reference to the accompanying drawings. The following embodiments exemplary describe a radiation treatment system including a treatment plan apparatus as a support apparatus, but is not limited to the following description. Specifically, the support apparatus according to the present application may be achieved by any apparatus included in the radiation treatment system described below. The support apparatus according to the present application may be achieved as a apparatus different from any apparatus included in the radiation treatment system described below.

Figure 1:
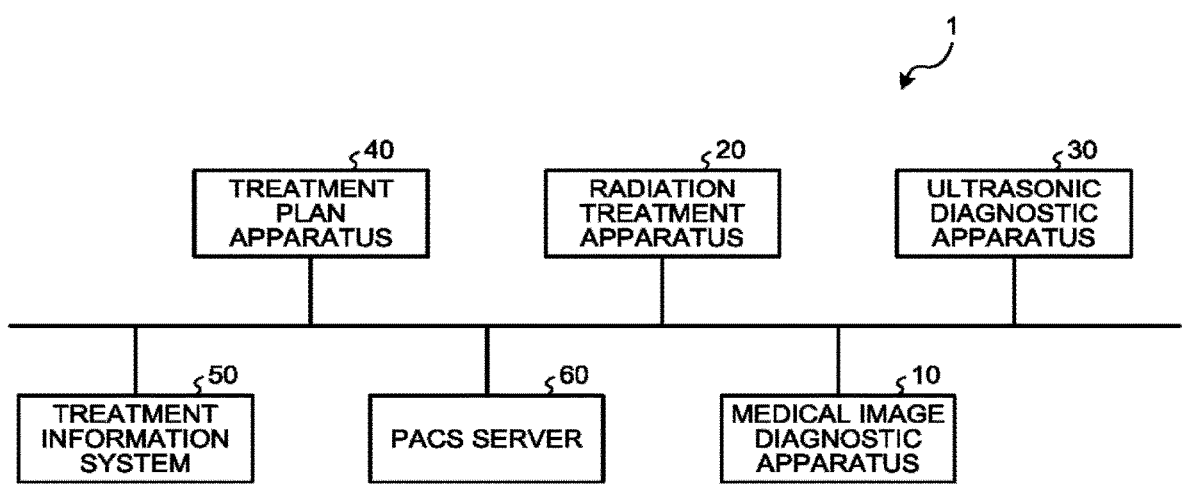
FIG. 1 is a diagram illustrating an exemplary configuration of a radiation treatment system according to a first embodiment.

The following first describes an exemplary configuration of a radiation treatment system 1 according to a first embodiment. FIG. 1 is a diagram illustrating an exemplary configuration of the radiation treatment system 1 according to the first embodiment. For example, as illustrated in FIG. 1, the radiation treatment system 1 includes a medical image diagnostic apparatus 10, a radiation treatment apparatus 20, an ultrasonic diagnostic apparatus 30, a treatment plan apparatus 40, a treatment information system 50, and a picture archiving and communication systems (PACS) server 60, which are mutually connected. In the radiation treatment system 1 according to the first embodiment, the treatment plan apparatus 40 acquires medical image data from the medical image diagnostic apparatus 10, prepares a treatment plan of radiation treatment on a target site (hereinafter referred to as a treatment target site) as a radiation treatment target, and transmits the treatment plan to the radiation treatment apparatus 20. The treatment plan apparatus 40 supports disposition of, on a subject, an ultrasonic probe for scanning the treatment target site on the basis of the treatment plan. The treatment plan apparatus 40 also executes display control to display various kinds of information on a display disposed in, for example, an operation room in which the radiation treatment is executed, and executes management of the entire radiation treatment in the radiation treatment system 1. The treatment information system 50 manages patient data and a treatment history. The PACS server 60 stores therein medical image data acquired by the medical image diagnostic apparatus 10 and performs various kinds of image processing on the medical image data. The configuration illustrated in FIG. 1 is merely exemplary, and the embodiment is not limited thereto. For example, a apparatus that executes display control and a apparatus that executes radiation treatment management may be separately provided.

Figure 2:
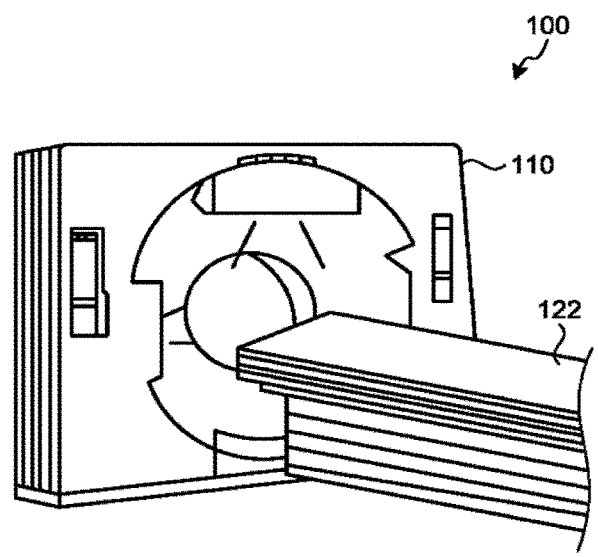
FIG. 2 is a diagram illustrating an exemplary radiation treatment plan CT apparatus according to the first embodiment.

The medical image diagnostic apparatus 10 is a apparatus for acquiring medical image data used to prepare a treatment plan. The medical image diagnostic apparatus 10 is, for example, an X-ray computed tomography (CT) apparatus, a magnetic resonance imaging (MRI) apparatus, an X-ray angiography apparatus, a positron emission tomography (PET) apparatus, or a single photon emission computed tomography (SPECT) apparatus. The following describes a radiation treatment plan CT apparatus 100 illustrated in FIG. 2 as an example of the medical image diagnostic apparatus 10. FIG. 2 is a diagram illustrating an exemplary radiation treatment plan CT apparatus 100 according to the first embodiment. As illustrated in FIG. 2, the radiation treatment plan CT apparatus 100 includes a gantry 110 and a couch device including a tabletop 122. The radiation treatment plan CT apparatus 100 acquires CT projection data including a treatment target site of a subject lying on the tabletop 122 and transmits reconstructed CT image data to the treatment plan apparatus 40.

Figure 3:
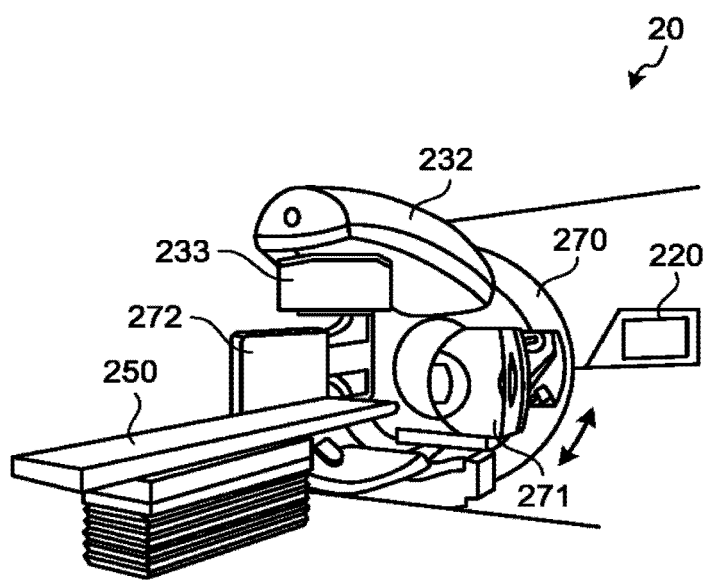
FIG. 3 is a diagram illustrating an exemplary radiation treatment apparatus according to the first embodiment.

The radiation treatment apparatus 20 executes radiation treatment on the subject on the basis of a treatment plan prepared by the treatment plan apparatus 40. The radiation treatment apparatus 20 will be described below with reference to FIG. 3. FIG. 3 is a diagram illustrating an exemplary radiation treatment apparatus 20 according to the first embodiment. As illustrated in FIG. 3, the radiation treatment apparatus 20 includes a rotational gantry 270, a couch device including a tabletop 250, a radiation generator 232 for emitting treatment radiation, and a collimator 233. The radiation treatment apparatus 20 irradiates a treatment target site with radiation according to a treatment plan forwarded from the treatment plan apparatus 40.

When the treatment target site is a moving site (for example, a liver) due to breathing and the like, for example, the radiation treatment apparatus 20 can irradiate the treatment target site having reached an irradiation position. For example, the radiation treatment apparatus 20 irradiates the treatment target site being at the irradiation position, while checking the position and motion of the treatment target site by using ultrasonic images acquired by the ultrasonic diagnostic apparatus 30 during radiation treatment.

The radiation treatment apparatus 20 may include a medical image acquisition apparatus for acquiring medical images for correcting the position of the subject in treatment preparation. For example, as illustrated in FIG. 3, the radiation treatment apparatus 20 may further include an XVI (Cone-Beam CT kV imaging apparatus) including a radiation generator 271 for emitting imaging radiation and a detector 272 for detecting imaging radiation, and may generate a positioning cone-beam CT image.

For example, before radiation treatment, the radiation treatment apparatus 20 rotates the rotational gantry 270 once, during which the radiation generator 271 continuously irradiates the subject to receive radiation having transmitted through the subject at the detector 272. This generates acquisition images (two-dimensional images) of the subject, viewed from various directions. Then, a cone-beam CT image is reconstructed on the basis of a plurality of acquisition images thus generated, and is displayed on a display 220. Registration is performed between this cone-beam CT image and the treatment plan CT image data to change the treatment plan so that the treatment plan CT image data is converted to match with the cone-beam CT image, thereby achieving accurate treatment targeted to the position of the treatment target site.

The ultrasonic diagnostic apparatus 30 acquires ultrasonic images including the treatment target site. For example, the ultrasonic diagnostic apparatus 30 acquires ultrasonic image data including the treatment target site data in real time while the radiation generator 232 included in the radiation treatment apparatus 20 is emitting treatment radiation. The ultrasonic diagnostic apparatus 30 transmits the ultrasonic images to the radiation treatment apparatus 20 and presents an ultrasonic image generated from the ultrasonic image data to an operator.

In the radiation treatment system 1, registration is performed in advance among a coordinate system of the radiation treatment plan CT apparatus 100, a coordinate system of the radiation treatment apparatus 20, and a coordinate system of the ultrasonic diagnostic apparatus 30. For example, in the radiation treatment system 1, infrared trace devices are respectively installed in a room in which the radiation treatment plan CT apparatus 100 is installed and a room in which the radiation treatment apparatus 20 is installed, and approximate registration is performed between coordinate systems thereof by using a laser sight installed in each room.

In addition, in the radiation treatment system 1, registration is performed between a treatment plan CT image, a cone-beam CT image, and an ultrasonic image to associate the coordinate system of the radiation treatment plan CT apparatus 100, the coordinate system of the radiation treatment apparatus 20, and the coordinate system of the ultrasonic diagnostic apparatus 30 with each other. For example, in the radiation treatment system 1, the coordinate system of the radiation treatment plan CT apparatus 100 and the coordinate system of the radiation treatment apparatus 20 are associated with each other by specifying, on the treatment plan CT image, a feature point identical to an anatomical feature point in the cone-beam CT image. In addition, in the radiation treatment system 1, ultrasonic images of a subject P are acquired by an ultrasonic probe including a sensor for acquiring position information and angle information, and a feature point identical to an anatomical feature point in the cone-beam CT image is specified on ultrasonic image data. And a coordinate system of each ultrasonic image, which is determined by the position and angle of the sensor, is associated with the coordinate system of the radiation treatment apparatus 20. The coordinate system of the radiation treatment plan CT apparatus 100 and the coordinate system of the radiation treatment apparatus 20 are associated with each other to allow the radiation treatment apparatus 20 to accurately determine a treatment position. In addition, the coordinate system of the radiation treatment apparatus 20 and the coordinate system of the ultrasonic diagnostic apparatus 30 are associated with each other to allow determination of whether a target tumor is located at a treatment position determined by the radiation treatment apparatus 20.

The treatment plan apparatus 40 prepares a treatment plan of radiation treatment performed by the radiation treatment apparatus 20, by using CT image data of the subject acquired by the radiation treatment plan CT apparatus 100. For example, the treatment plan apparatus 40 specifies the position of a treatment target site inside the subject by using the CT image data acquired by the radiation treatment plan CT apparatus 100. For example, the treatment plan apparatus 40 prepares a plan including a dose, irradiation angle, and irradiation number of radiation emitted by the radiation treatment apparatus 20 for a tumor, the position of which is specified by using the CT image data.

Then, the treatment plan apparatus 40 presents the prepared treatment plan (including an irradiation condition and a dose map of irradiation of the subject) to the operator. The operator determines whether the content of the treatment plan is appropriate by determining whether an exposure amount of the subject is in an allowable range or whether the effect of the radiation treatment can be sufficiently obtained when radiation treatment is executed in accordance with the treatment plan. If the operator determines that the treatment plan is inappropriate, the treatment plan apparatus 40 prepares a treatment plan again. If the operator determines that the treatment plan is appropriate, the treatment plan apparatus 40 transmits the treatment plan to the radiation treatment apparatus 20.

The treatment plan apparatus 40 also determines whether radiation treatment performed by the radiation treatment apparatus 20 is to be performed with ultrasonic guide provided by the ultrasonic diagnostic apparatus 30. For example, the treatment plan apparatus 40 displays buttons indicating "Yes" and "No" in a GUI dialogue box presented to the operator through the display, and determines whether the ultrasonic guide is provided depending on pressing on the buttons. Alternatively, for example, the treatment plan apparatus 40 may determine whether the ultrasonic guide is provided depending on whether a GUI check box presented to the operator through the display is checked.

If it is determined that radiation treatment is to be performed with the ultrasonic guide, the treatment plan apparatus 40 calculates, on the basis of the treatment plan, the recommendation degree of disposition of an ultrasonic probe that scans the treatment target site in the radiation treatment, for each position in the subject, and notifies the operator of the calculated recommendation degree in association with the position in the subject. That is, the treatment plan apparatus 40 supports disposition of the ultrasonic probe on the subject to execute the ultrasonic guide. This will be described later.

The radiation treatment apparatus 20 corrects the treatment plan so that the treatment target site can be accurately targeted, by performing registration between medical images acquired by the medical image acquisition apparatus such as an XVI included in the radiation treatment apparatus 20 and CT image data acquired by the radiation treatment plan CT apparatus 100. In other words, the radiation treatment apparatus 20 accurately determines the position of the treatment target site in a space in which the radiation treatment is performed, by performing registration between the medical images acquired by the medical image acquisition apparatus such as an XVI and the CT image data acquired by the radiation treatment plan CT apparatus 100, and performs the treatment in accordance with the determined position.

The configuration of the radiation treatment system 1 illustrated in FIG. 1 is merely exemplary and may include various kinds of other apparatuses. For example, the radiation treatment system 1 may include a position check device for detecting change in the position of the subject due to body motion, and may further include various kinds of systems such as a radiology information system (RIS) and a hospital information system (HIS).

Figure 4:
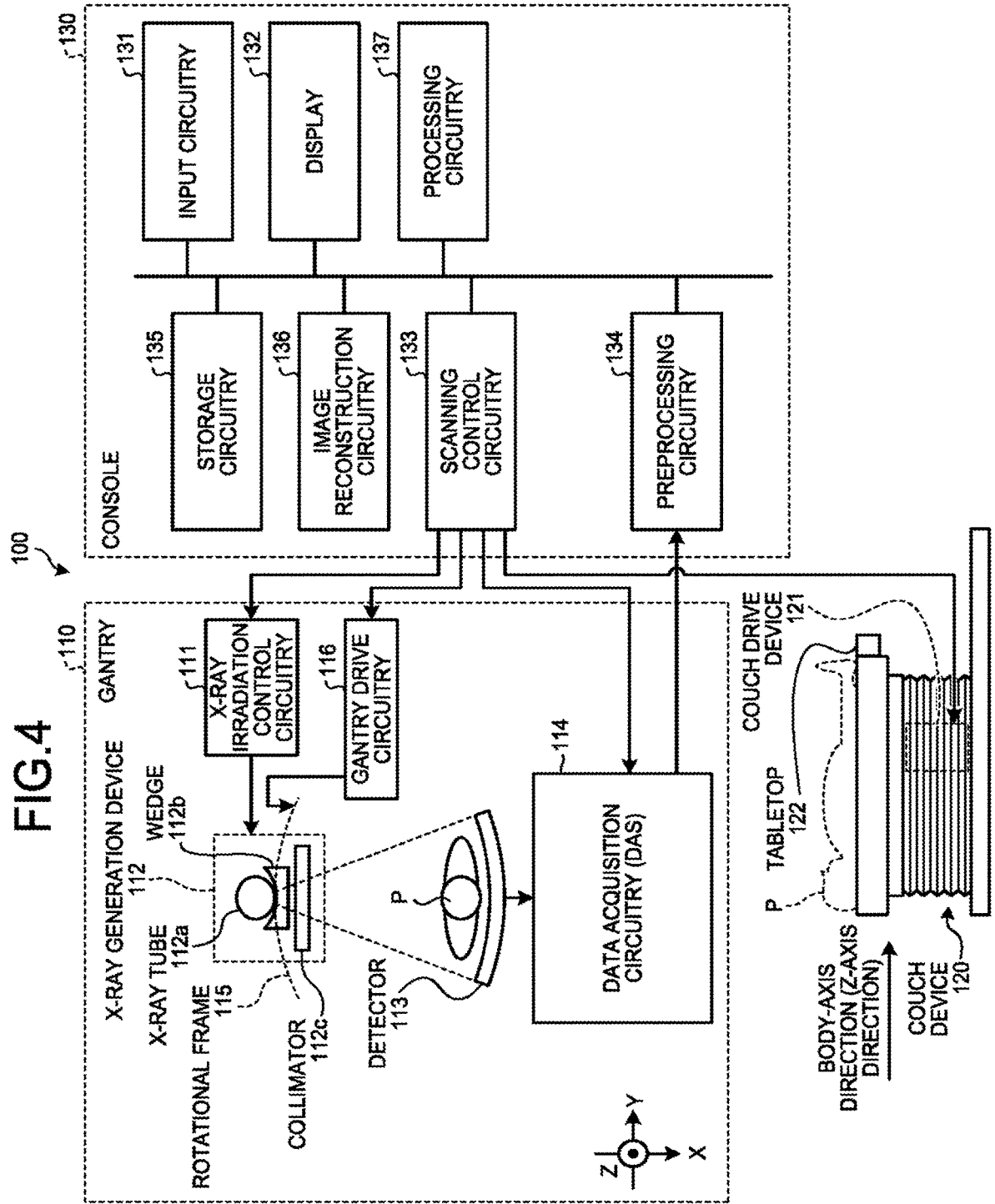
FIG. 4 is a diagram illustrating an exemplary configuration of the radiation treatment plan CT apparatus according to the first embodiment.

The following describes each apparatus in the radiation treatment system 1. FIG. 4 is a diagram illustrating an exemplary configuration of the radiation treatment plan CT apparatus 100 according to the first embodiment. As illustrated in FIG. 4, the radiation treatment plan CT apparatus 100 includes the gantry 110, a couch device 120, and a console 130.

The gantry 110 is a device that irradiates the subject P (patient) with X-ray, detects X-ray transmitting through the subject P, and outputs a result of the detection to the console 130. The gantry 110 includes X-ray irradiation control circuitry 111, an X-ray generation device 112, a detector 113, data acquisition circuitry (data acquisition system (DAS)) 114, a rotational frame 115, and gantry drive circuitry 116.

The rotational frame 115 is a circular frame that supports the X-ray generation device 112 and the detector 113 facing each other with the subject P interposed therebetween and is driven by the gantry drive circuitry 116 to rotate at high speed in a circular orbit centered on the subject P. The X-ray irradiation control circuitry 111 controls a high voltage generator (not illustrated) to supply an X-ray tube 112a with high voltage. The X-ray irradiation control circuitry 111 adjusts the amount of X-ray irradiated to the subject P by adjusting tube voltage supplied to the X-ray tube 112a and tube current under control of scanning control circuitry 133. The X-ray irradiation control circuitry 111 performs switching of a wedge 112b. The X-ray irradiation control circuitry 111 adjusts an irradiation range (fan angle and cone angle) of X-ray by adjusting the opening degree of a collimator 112c.

The X-ray generation device 112 generates X-ray and irradiates the subject P with the generated X-ray, and includes the X-ray tube 112a, the wedge 112b, and the collimator 112c. The X-ray tube 112a is a vacuum tube that generates, under control of the X-ray irradiation control circuitry 111, X-ray by using high voltage supplied from the high voltage generator (not illustrated), and irradiates the subject P with an X-ray beam as the rotational frame 115 rotates. The wedge 112b is an X-ray filter for adjusting, under control of the X-ray irradiation control circuitry 111, the amount of X-ray emitted from the X-ray tube 112a. Specifically, the wedge 112b is a filter for transmitting and attenuating X-ray emitted from the X-ray tube 112a so that the X-ray emitted from the X-ray tube 112a to the subject P has a predetermined distribution. The wedge 112b is also called a wedge filter or a bow-tie filter.

The collimator 112c is a slit for narrowing down, under control of the X-ray irradiation control circuitry 111, the irradiation range of X-ray, the amount of which is adjusted by the wedge 112b. The gantry drive circuitry 116 rotates, by rotating the rotational frame 115, the X-ray generation device 112 and the detector 113 in a circular orbit centered on the subject P. The detector 113 is a two-dimensional array detector (planar detector) that detects X-ray transmitting through the subject P and including a plurality of detection element rows arrayed along a body-axis direction (Z-axis direction illustrated in FIG. 4) of the subject P, each detection element row including X-ray detection elements arranged for a plurality of channels.

The data acquisition circuitry 114 is a DAS that acquires CT projection data from detection data of X-ray detected by the detector 113. For example, the data acquisition circuitry 114 generates CT projection data by performing, for example, amplification processing, A/D conversion processing, and inter-channel sensitivity correction processing on X-ray intensity distribution data detected by the detector 113, and transmits the generated CT projection data to the console 130. For example, while X-ray is continuously emitted from the X-ray tube 112a as the rotational frame 115 rotates, the data acquisition circuitry 114 acquires a set of CT projection data for the entire circumference (360°). The data acquisition circuitry 114 transmits each acquired CT projection data to the console 130 in association with the position of the tube. The position of the tube is information indicating a projection direction of the CT projection data.

The couch device 120 is a device on which the subject P is placed, and includes a couch drive device 121 and the tabletop 122. The couch drive device 121 moves the subject P into the rotational frame 115 by moving the tabletop 122 in the Z-axis direction. The tabletop 122 is a board on which the subject P is placed. A typical CT tabletop has a centrally recessed shape for fitting to the body of a patient, but in the radiation treatment plan CT apparatus 100, the tabletop 122 has a shape similarly to that of the tabletop 250 of the radiation treatment apparatus 20.

The console 130 is a device that receives an operation on the radiation treatment plan CT apparatus 100 by the operator and reconstructs CT image data (volume data) by using the CT projection data acquired by the gantry 110. As illustrated in FIG. 4, the console 130 includes input circuitry 131, a display 132, the scanning control circuitry 133, preprocessing circuitry 134, storage circuitry 135, image reconstruction circuitry 136, and processing circuitry 137.

The input circuitry 131 includes a mouse, a keyboard, a track ball, a switch, a button, and a joystick, which are used by the operator of the radiation treatment plan CT apparatus 100 to input various instructions and various settings, and forwards information on instructions and settings received from the operator to the processing circuitry 137. The display 132 is a monitor referred to by the operator and displays, under control of the processing circuitry 137, part of CT image data to the operator, and displays a graphical user interface (GUI) for receiving, for example, various instructions and various settings from the operator through the input circuitry 131.

The scanning control circuitry 133 controls processing performed by the gantry 110 to acquire the CT projection data, by controlling operation of the X-ray irradiation control circuitry 111, the gantry drive circuitry 116, the data acquisition circuitry 114, and the couch drive device 121 under control of the processing circuitry 137. Specifically, the scanning control circuitry 133 controls the processing of acquiring the CT projection data at acquiring radiation treatment plan CT image data.

The preprocessing circuitry 134 generates corrected CT projection data by performing, on the CT projection data generated by the data acquisition circuitry 114, correction processing such as logarithmic conversion processing, offset correction, sensitivity correction, and beam hardening correction, and stores the corrected CT projection data in the storage circuitry 135. The storage circuitry 135 stores therein the CT projection data generated by the preprocessing circuitry 134. The storage circuitry 135 also stores therein CT image data generated by the image reconstruction circuitry 136.

The image reconstruction circuitry 136 reconstructs CT image data (volume data) by using the CT projection data stored in the storage circuitry 135. This reconstruction may be achieved by various kinds of methods including back projection processing. The back projection processing may be achieved by, for example, a filtered back projection (FBP) method. Alternatively, the image reconstruction circuitry 136 may reconstruct the CT image data by an iterative approximation method. Then, the image reconstruction circuitry 136 stores the reconstructed CT image data in the storage circuitry 135 and also transmits the reconstructed CT image data to the treatment plan apparatus 40.

The processing circuitry 137 performs entire control of the radiation treatment plan CT apparatus 100 by controlling operation of the gantry 110, the couch device 120, and the console 130. Specifically, the processing circuitry 137 controls CT scanning performed by the gantry 110 through control of the scanning control circuitry 133. The processing circuitry 137 also performs control to generate display CT image from the CT image data stored in the storage circuitry 135 and to display the generated display CT image on the display 132.

A processing function achieved by each circuitry illustrated in FIG. 4 is recorded in the storage circuitry 135 in the format of a computer-executable program. Each circuitry is a processor that reads the corresponding computer program from the storage circuitry 135 and executes the computer program to achieve the function corresponding to the computer program.

Figure 5:
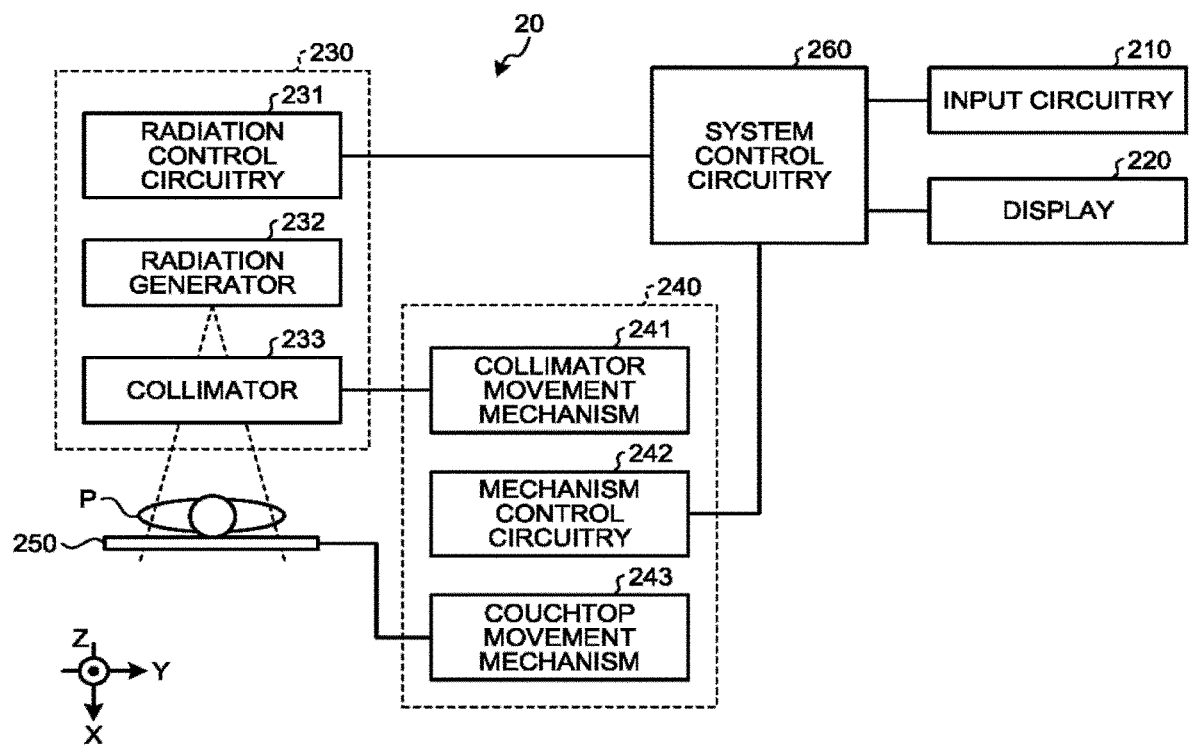
FIG. 5 is a diagram illustrating an exemplary configuration of the radiation treatment apparatus according to the first embodiment.

FIG. 5 is a diagram illustrating an exemplary configuration of the radiation treatment apparatus 20 according to the first embodiment. As illustrated in FIG. 5, the radiation treatment apparatus 20 includes input circuitry 210, the display 220, a radiation generation device 230, a moving mechanism 240, the tabletop 250, and system control circuitry 260. The radiation generation device 230 includes radiation control circuitry 231, the radiation generator 232, and the collimator 233. The radiation control circuitry 231 controls, under control of the system control circuitry 260, for example, an applied voltage and an application time at the high voltage generator of the radiation generator 232 to achieve irradiation with the amount of radiation according to a treatment plan. The radiation generator 232 includes an electron gun and an acceleration tube (not illustrated). The acceleration tube accelerates a thermion generated from the electron gun and causes the thermion to collide with a tungsten target to emit treatment radiation. The collimator 233 is, for example, a multi-leaf collimator (MLC) including a plurality of blades for setting the irradiation range of the treatment radiation. For example, the collimator 233 forms a radiation region having a shape corresponding to a treatment target site of the subject P by moving these blades through a collimator moving mechanism 241.

The moving mechanism 240 includes the collimator moving mechanism 241, mechanism control circuitry 242, and a tabletop moving mechanism 243. The collimator moving mechanism 241 moves the blades of the collimator 233 under control of the mechanism control circuitry 242. The tabletop moving mechanism 243 moves the tabletop 250 under control of the mechanism control circuitry 242. The mechanism control circuitry 242 moves, under control of the system control circuitry 260, the blades by transmitting a blades movement control signal to the collimator moving mechanism 241. The mechanism control circuitry 242 moves the tabletop 250 by transmitting a tabletop movement control signal to the tabletop moving mechanism 243.

The input circuitry 210 includes a mouse, a keyboard, a track ball, a switch, a button, and a joystick, which are used by the operator of the radiation treatment apparatus 20 to input various instructions and various settings, and forwards information on instructions and settings received from the operator to the system control circuitry 260. The display 220 is a monitor referred to by the operator and displays, under control of the system control circuitry 260, a cone-beam CT image to the operator, and displays a GUI for receiving, for example, various instructions and various settings from the operator through the input circuitry 210.

The system control circuitry 260 performs entire control of the radiation treatment apparatus 20 by controlling operation of the rotational gantry 270, the radiation generation device 230, and the moving mechanism 240. Specifically, the system control circuitry 260 controls irradiation of the subject P with radiation by controlling the radiation control circuitry 231 on the basis of a treatment plan received from the treatment plan apparatus 40. The system control circuitry 260 controls the position of the tabletop 250 by controlling the mechanism control circuitry 242 on the basis of the treatment plan. The system control circuitry 260 controls display of a cone-beam CT image and a GUI on the display 220. The radiation treatment apparatus 20 includes storage circuitry (not illustrated), and stores therein the treatment plan forwarded from the treatment plan apparatus 40 in the storage circuitry. Then, the system control circuitry 260 reads the treatment plan from the storage circuitry, and executes the above-described control.

A processing function achieved by each circuitry illustrated in FIG. 5 is recorded in the storage circuitry (not illustrated) in the format of a computer-executable program. Each circuitry is a processor that reads the corresponding computer program from the storage circuitry (not illustrated) and executes the computer program to achieve the function corresponding to the computer program.

Figure 6:
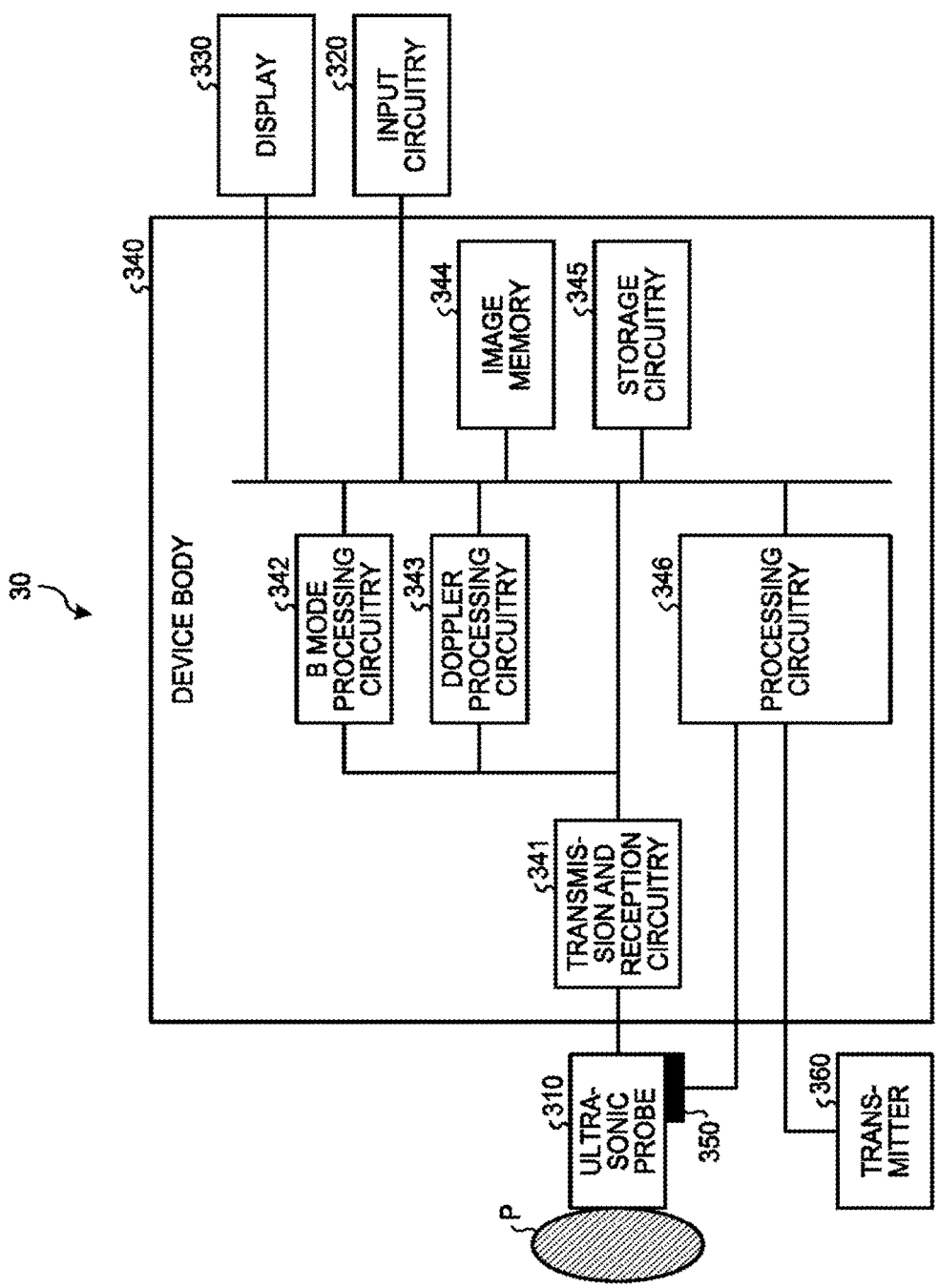
FIG. 6 is a diagram illustrating an exemplary configuration of an ultrasonic diagnostic apparatus according to the first embodiment.

FIG. 6 is a diagram illustrating an exemplary configuration of the ultrasonic diagnostic apparatus 30 according to the first embodiment. As illustrated in FIG. 6, the ultrasonic diagnostic apparatus 30 according to the first embodiment includes an ultrasonic probe 310, input circuitry 320, a display 330, a device body 340, a sensor 350, and a transmitter 360.

The ultrasonic probe 310 includes a plurality of piezoelectric transducer elements that generate ultrasonic waves on the basis of a drive signal supplied from transmission and reception circuitry 341. The ultrasonic probe 310 receives the reflected waves from the subject P and converts the received waves into an electric signal. The ultrasonic probe 310 includes a matching layer provided to the piezoelectric transducer elements, and, for example, a backing material for preventing backward traveling of ultrasonic waves from the piezoelectric transducer elements.

For example, when ultrasonic waves are transmitted from the ultrasonic probe 310 to the subject P, the transmitted ultrasonic waves are sequentially reflected at discontinuous surfaces of acoustic impedance in a body tissue of the subject P, and received as a reflected wave signal by the piezoelectric transducer elements included in the ultrasonic probe 310. The amplitude of the reflected wave signal thus received depends on a difference in acoustic impedance across the discontinuous surfaces at which the ultrasonic waves are reflected. A reflected wave signal generated when a transmitted ultrasonic pulse is reflected at moving blood current and, for example, the surface of a cardiac wall suffers a frequency shift due to the Doppler effect depending on a speed component of a moving body in an ultrasonic wave transmission direction.

The ultrasonic probe 310 is a 2D probe capable of performing three-dimensional ultrasonic scanning of the subject P through a plurality of piezoelectric transducer elements arranged in a matrix. Alternatively, the ultrasonic probe 310 is a 3D probe capable of performing three-dimensional scanning of the subject P by swinging a plurality of linearly arranged piezoelectric transducer elements by a predetermined angle (swing angle) while performing two-dimensional scanning of the subject P through the piezoelectric transducer elements.

The ultrasonic probe 310 may have a wired configuration or a wireless configuration. With the wired configuration, the ultrasonic probe 310 includes a probe body, a connection terminal, a connector, and a cable. The probe body includes a plurality of piezoelectric transducer elements and performs the above-described transmission and reception of ultrasonic waves. The connection terminal connects, to the device body 340, a signal line through which a transmission signal to the probe body and a received signal from the probe body are communicated. The connector houses therein the cable and establishes electrical connection by fixing the ultrasonic probe 310 to the device body 340. The cable is a cable for communicating a signal between the probe body and the device body 340. For example, the cable includes a plurality of signal lines each connected with the device body 340 through the connection terminal.

With the wireless configuration, the ultrasonic probe 310 and the device body 340 each include wireless communication circuitry that executes wireless communication, and communicates, through a radio signal, for example, a control signal related to connection between the ultrasonic probe 310 and the device body 340 or a control signal related to transmission and reception of ultrasonic waves. In this case, the ultrasonic probe 310 includes a plurality of piezoelectric transducer elements and a probe body that performs the above-described transmission and reception of ultrasonic waves. In other words, with the wireless configuration, the ultrasonic probe 310 does not include the connection terminal, the connector, and the cable described above.

As illustrated in FIG. 6, the sensor 350 is attached to the ultrasonic probe 310 (probe body), and the transmitter 360 is disposed at an optional position near the device body 340. The transmitter 360 is a device that forms a magnetic field outwardly from the transmitter 360. The sensor 350 detects the magnitude and gradient of a three-dimensional magnetic field formed by the transmitter 360. Then, the sensor 350 calculates the position and angle of the sensor 350 in a space the origin of which is at the transmitter 360 on the basis of the detected information of the magnetic field, and transmits the calculated position and angle to the device body 340.

In this manner, when the ultrasonic probe 310 includes the sensor 350, the radiation treatment system 1 can uniquely identify the position and angle of the ultrasonic probe 310 in a three-dimensional coordinate system of ultrasonic image data on the basis of a reflected wave signal received by the piezoelectric transducer elements. Registration is performed in advance among the coordinate systems of the radiation treatment plan CT apparatus 100, the radiation treatment apparatus 20, and the ultrasonic diagnostic apparatus 30, and thus the radiation treatment system 1 can uniquely identify the position and angle of the ultrasonic probe 310 on CT image data acquired by the radiation treatment plan CT apparatus 100, or the position and angle of the ultrasonic probe 310 with respect to the subject P being subjected to radiation treatment performed by the radiation treatment apparatus 20.

The ultrasonic probe 310 is fixed to the subject P through a fixer (not illustrated). For example, the fixer is a holder stably placed on the tabletop on which the subject P is placed, and fixes the ultrasonic probe 310 to the subject P. For example, the fixer is a holder including an arm including one or a plurality of joints and fixes the ultrasonic probe 310 at an optional angle at an optional position on the subject P.

The input circuitry 320 includes a mouse, a keyboard, a button, a panel switch, a touch command screen, a foot switch, a track ball, or a joystick, and receives various setting requests from the operator of the ultrasonic diagnostic apparatus 30 and forwards the received various setting requests to the device body 340. The display 330 displays a GUI for allowing the operator of the ultrasonic diagnostic apparatus 30 to input various setting requests by using the input circuitry 320, and displays, for example, various kinds of image data generated by the device body 340.

As illustrated in FIG. 6, the device body 340 includes the transmission and reception circuitry 341, B mode processing circuitry 342, Doppler processing circuitry 343, an image memory 344, storage circuitry 345, and processing circuitry 346. The transmission and reception circuitry 341 includes a pulse generator, transmission delay circuitry, and a pulser, and supplies a drive signal to the piezoelectric transducer elements. The pulse generator repeatedly generates a rate pulse for forming transmission ultrasonic waves at a predetermined rate frequency. The transmission delay circuitry focuses ultrasonic waves generated from the piezoelectric transducer elements into a beam, and provides a delay time for each piezoelectric transducer element, which is necessary for determining transmission directionality, to each rate pulse generated by the pulse generator. The pulser applies a drive signal (drive pulse) to the piezoelectric transducer elements at a timing based on the rate pulse. Accordingly, the transmission delay circuitry changes the delay time provided to each rate pulse to optionally adjust a transmission direction of ultrasonic waves transmitted from a piezoelectric transducer element plane.

The transmission and reception circuitry 341 has a function that allows instantaneous change of, for example, a transmission frequency and a transmission drive voltage to execute a predetermined scanning sequence on the basis of an instruction from the processing circuitry 346. In particular, the change of the transmission drive voltage is achieved by linear amplifier oscillation circuitry having an instantaneously switchable value, or a mechanism that electrically switches a plurality of power units.

The transmission and reception circuitry 341 includes a preamplifier, an analog/digital (A/D) converter, reception delay circuitry, and an adder, and generates reflected wave data by performing various kinds of processing on a reflected wave signal received by the piezoelectric transducer elements. The preamplifier amplifies the reflected wave signal for each channel. The A/D converter performs A/D conversion of the amplified reflected wave signal. The reception delay circuitry provides a delay time necessary for determining reception directionality. The adder generates the reflected wave data by performing addition processing on the reflected wave signal processed by the reception delay circuitry. The addition processing performed by the adder enhances a reflection component in a direction in accordance with the reception directionality of the reflected wave signal, and forms a beam comprehensive for transmission and reception of ultrasonic waves on the basis of the reception directionality and the transmission directionality. An output signal from the transmission and reception circuitry 341 may be selected in various kinds of formats such as a format as a signal called a radio frequency (RF) signal including phase information, or as amplitude information after envelope detection processing.

The B mode processing circuitry 342 receives the reflected wave data from the transmission and reception circuitry 341 and performs, for example, logarithmic amplification and envelope detection processing on the reflected wave data to generate data (B mode data) in which signal strength is expressed in the brightness of luminance. The Doppler processing circuitry 343 performs frequency analysis on speed information from the reflected wave data received from the transmission and reception circuitry 341, extracts blood current, tissue, contrast dye echo components due to the Doppler effect, and generates data (Doppler data) obtained by extracting moving body information such as speed, dispersion, and power at multiple points.

The B mode processing circuitry 342 and the Doppler processing circuitry 343 are capable of processing three-dimensional reflected wave data. Specifically, the B mode processing circuitry 342 generates three-dimensional B mode data from three-dimensional reflected wave data. The Doppler processing circuitry 343 generates three-dimensional Doppler data from three-dimensional reflected wave data. The three-dimensional B mode data is data in which a luminance value is allocated in accordance with reflection strength of a reflection source positioned at each of a plurality of points (sample points) set on each scanning line in a three-dimensional scanning range. The three-dimensional Doppler data is data in which a luminance value is allocated in accordance with a value of blood current information (speed, dispersion, and power) at each of a plurality of points (sample points) set on each scanning line in the three-dimensional scanning range.

The image memory 344 stores therein image data generated by the processing circuitry 346. The image memory 344 may store therein data generated by the B mode processing circuitry 342 and the Doppler processing circuitry 343. The storage circuitry 345 stores therein various kinds of data of, for example, a control program for performing transmission and reception of ultrasonic waves, image processing, and display processing. The storage circuitry 345 is used for, for example, storage of image data stored in the image memory 344, as necessary.

The processing circuitry 346 controls the entire processing of the ultrasonic diagnostic apparatus 30. For example, the processing circuitry 346 generates ultrasonic image data from data generated by the B mode processing circuitry 342 and the Doppler processing circuitry 343. Specifically, the processing circuitry 346 generates B mode image data in which a luminance is expressed in the strength of reflected waves from B mode data generated by the B mode processing circuitry 342. The B mode image data is data in which the shape of a tissue inside a region scanned with ultrasonic waves is visualized. The processing circuitry 346 generates Doppler image data indicating the moving body information from the Doppler data generated by the Doppler processing circuitry 343. The Doppler image data is speed image data, dispersion image data, power image data, or image data that is a combination of these types of image data. Specifically, the Doppler image data indicates fluid information related to fluid flowing inside the region scanned with ultrasonic waves.

The processing circuitry 346 typically generates a display ultrasonic image through conversion (scanning conversion) of a scanning line signal string of ultrasonic scanning into a scanning line signal string in a video format such as that of a television. Specifically, the processing circuitry 346 generates an ultrasonic image through coordinate conversion in accordance with the format of ultrasonic scanning by the ultrasonic probe 310. The processing circuitry 346 uses a plurality of image frames obtained through scanning conversion to perform, for example, image processing (smoothing processing) of regenerating an average luminance value image and image processing (edge enhancement processing) using a differential filter in an image.

In addition, the processing circuitry 346 generates three-dimensional B mode image data through coordinate conversion of the three-dimensional B mode data generated by the B mode processing circuitry 342. The processing circuitry 346 generates three-dimensional Doppler image data through coordinate conversion of the three-dimensional the Doppler data generated by the Doppler processing circuitry 343. The three-dimensional B mode data and the three-dimensional Doppler image data are volume data not processed through scanning conversion.

The processing circuitry 346 executes various kinds of control in the entire apparatus described above. For example, the processing circuitry 346 controls processing at the transmission and reception circuitry 341, the B mode processing circuitry 342, and the Doppler processing circuitry 343 on the basis of various setting requests input from the operator through the input circuitry 320 and various kinds of data read from the storage circuitry 345. The processing circuitry 346 transmits volume data to the treatment plan apparatus 40. The processing circuitry 346 generates a display ultrasonic image from volume data stored in the image memory 344 and the storage circuitry 345, and performs control to display the display ultrasonic image on the display 330.

A processing function achieved by each circuitry illustrated in FIG. 6 is recorded in the storage circuitry 345 in the format of a computer-executable program. Each circuitry is a processor that reads the corresponding computer program from the storage circuitry 345 and executes the computer program to achieve the function corresponding to the computer program.

Figure 7:
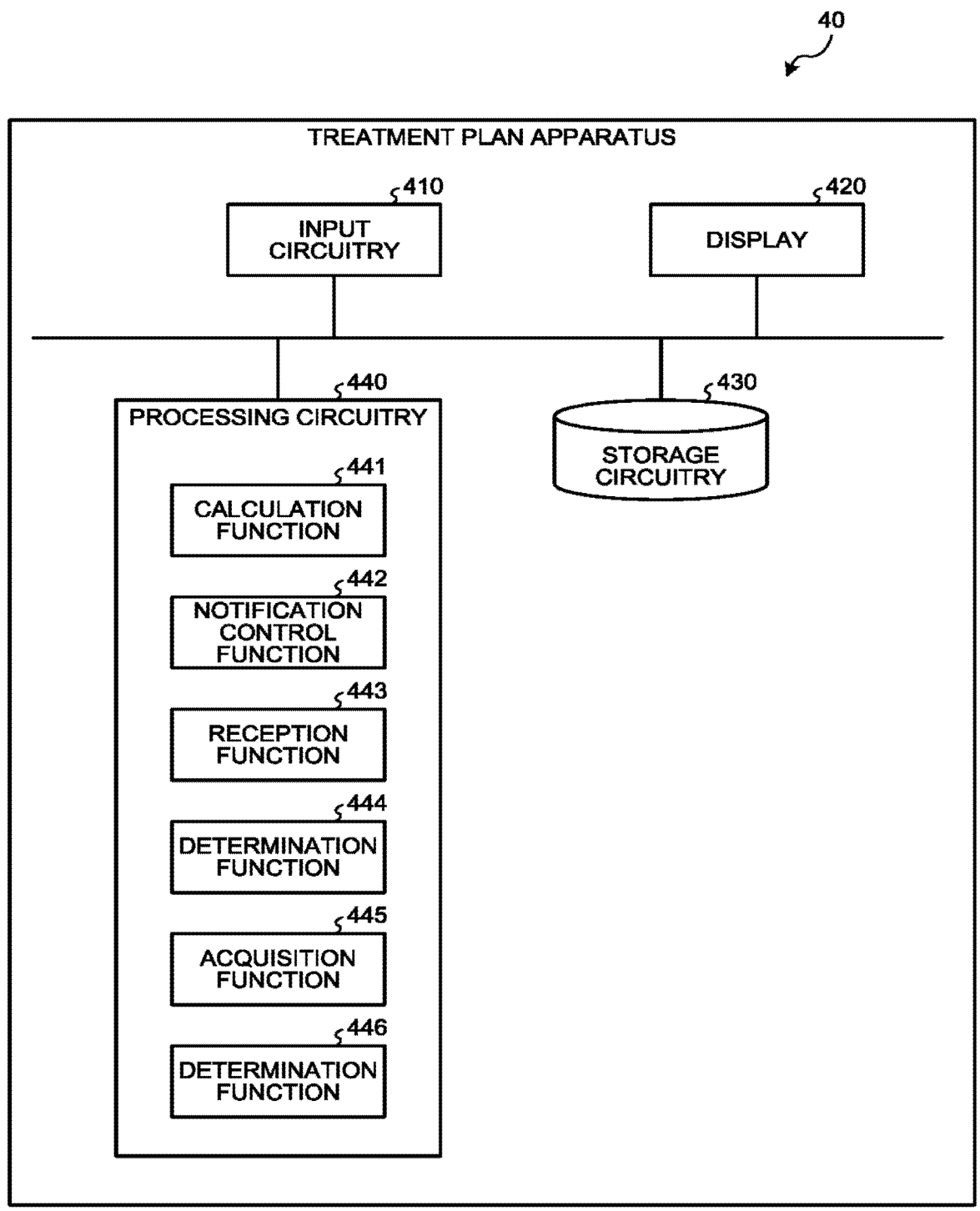
FIG. 7 is a diagram illustrating an exemplary configuration of a treatment plan apparatus according to the first embodiment.

FIG. 7 is a diagram illustrating an exemplary configuration of the treatment plan apparatus 40 according to the first embodiment. As illustrated in FIG. 7, the treatment plan apparatus 40 includes input circuitry 410, a display 420, storage circuitry 430, and processing circuitry 440. For example, the treatment plan apparatus 40 is a work station or an optional personal computer.

The input circuitry 410 is a pointing device such as a mouse or an input device such as a keyboard, and receives input of various operations on the treatment plan apparatus 40 from the operator. For example, the input circuitry 410 receives an operation to specify the treatment target site, on the CT image data acquired by the radiation treatment plan CT apparatus 100. For example, the input circuitry 410 receives a specifying operation to specify the position of the ultrasonic probe 310 in the subject P.

The display 420 is a display device, such as a liquid crystal display, and displays various kinds of information. For example, the display 420 displays a GUI for receiving various operations from the operator, a display CT image generated from the CT image data for a treatment plan, and a result of processing performed by the processing circuitry 440 to be described later. The treatment plan apparatus 40 may include a plurality of displays 420 that may be disposed in, for example, a room in which the operator prepares a treatment plan and a room in which the radiation treatment apparatus 20 is disposed.

The storage circuitry 430 is a semiconductor memory element such as a random access memory (RAM) or a flash memory, or a storage device such as a hard disk or an optical disk, and stores therein various computer programs read and executed by the processing circuitry 440 to be described later. For example, the storage circuitry 430 stores therein a treatment plan prepared by the processing circuitry 440. For example, the storage circuitry 430 stores therein, for each subject, an irradiation condition of radiation on the treatment target site, and information such as dose distribution and dose volume histogram calculated on the basis of the irradiation condition. The storage circuitry 430 may store therein exposure information for each subject. The storage circuitry 430 also stores therein a result of the processing performed by the processing circuitry 440 to be described later.

The processing circuitry 440 prepares a treatment plan of radiation treatment performed by the radiation treatment apparatus 20 by using the CT image data of the subject P acquired by the radiation treatment plan CT apparatus 100. For example, the processing circuitry 440 specifies the position of a treatment target site inside the subject P by using the CT image data acquired by the radiation treatment plan CT apparatus 100. For example, the processing circuitry 440 prepares a plan including a dose, an irradiation angle, and a number of times of irradiation, of radiation emitted by the radiation treatment apparatus 20 onto the treatment target site, the position of which is specified by using the CT image data. Then, the processing circuitry 440 stores the prepared treatment plan in the storage circuitry 430.

The processing circuitry 440 executes various kinds of processing at the treatment plan apparatus 40. For example, as illustrated in FIG. 7, the processing circuitry 440 performs various kinds of processing by reading, from the storage circuitry 430, computer programs corresponding to a calculation function 441, a notification control function 442, a reception function 443, a determination function 444, an acquisition function 445, and a determination function 446, and executing the computer programs. A processing function achieved by each circuitry illustrated in FIG. 7 is recorded in the storage circuitry 430 in the format of a computer-executable program. Each circuitry is a processor that reads the corresponding computer program from the storage circuitry 430 and executes the computer program to achieve the function corresponding to the computer program. The calculation function 441 illustrated in FIG. 7 corresponds to calculation processing performed by a processing circuitry in the claims. The notification control function 442 illustrated in FIG. 7 corresponds to notification control processing performed by the processing circuitry in the claims.

The treatment plan apparatus 40 supports, on the basis of a treatment plan, disposition of the ultrasonic probe 310 on the subject P in radiation treatment. Specifically, the treatment plan apparatus 40 supports disposition of the ultrasonic probe 310 in radiation treatment by calculating the recommendation degree of disposition of the ultrasonic probe 310 for each position in the subject P and notifying the operator of the calculated recommendation degree in association with the position in the subject P.

For example, the calculation function 441 first acquires an irradiation plan (treatment plan) of radiation onto a treatment target site in the subject P from the storage circuitry 430. The treatment plan acquired by the calculation function 441 includes three-dimensional CT image data of the subject P acquired by the radiation treatment plan CT apparatus 100. The calculation function 441 acquires, from the treatment plan, various kinds of information such as the irradiation range of radiation with which the treatment target site is irradiated, distribution of an ultrasonic medium between the ultrasonic probe 310 and the treatment target site, the distance between the ultrasonic probe 310 and the treatment target site, the degree of deformation of a contact surface of the subject P in contact with the ultrasonic probe 310, and an angle between the ultrasonic probe 310 scanning the treatment target site and the contact surface. Then, the calculation function 441 calculates, for each position in the subject P, the recommendation degree of a probe position of the ultrasonic probe 310 from various kinds of information on the basis of the irradiation plan with radiation. The notification control function 442 notifies the operator of the recommendation degree in association with a position in the subject P. This allows support of positioning of the ultrasonic probe 310 in radiation treatment.

Figure 8:
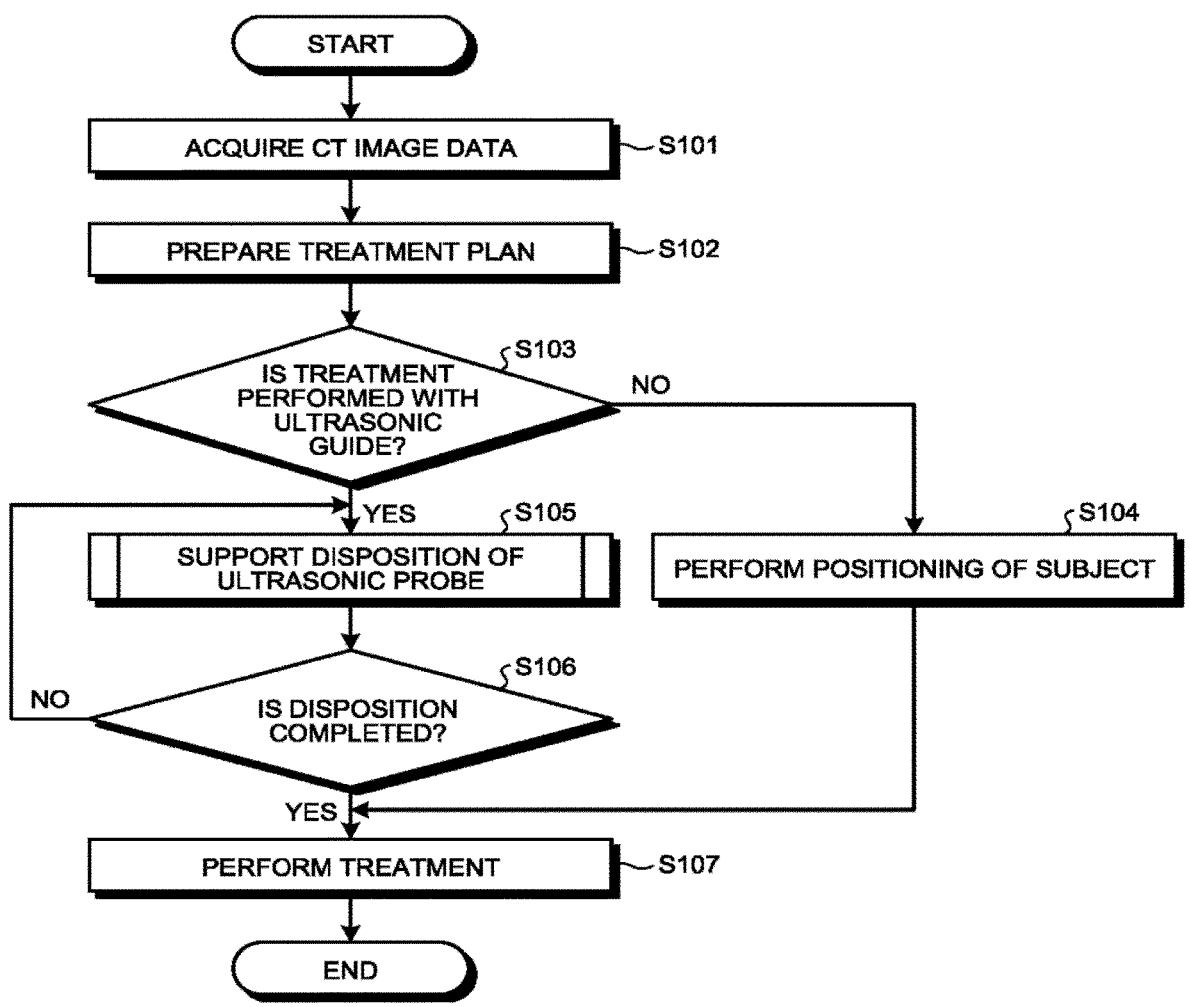
FIG. 8 is a flowchart illustrating an exemplary procedure of processing performed by a radiation treatment system according to the first embodiment.

The following describes exemplary processing performed by the radiation treatment system 1 according to the first embodiment with reference to FIG. 8. FIG. 8 is a flowchart illustrating an exemplary procedure of the processing performed by the radiation treatment system 1 according to the first embodiment. As illustrated in FIG. 8, in the radiation treatment system 1, first, the radiation treatment plan CT apparatus 100 acquires the CT image data (step S101) and transmits the acquired CT image data to the treatment plan apparatus 40. Then, the treatment plan apparatus 40 prepares a treatment plan (step S102) and transmits the treatment plan to the radiation treatment apparatus 20. The radiation treatment apparatus 20 executes commission of the treatment plan. In the commission of the treatment plan, it is commissioned by using, for example, a phantom and a dosemeter that irradiation with radiation can be performed according to the treatment plan, and it is visually determined whether interference occurs in the radiation treatment apparatus 20 or between the radiation treatment apparatus 20 and the subject P.

Subsequently, the treatment plan apparatus 40 determines whether radiation treatment performed by the radiation treatment apparatus 20 is to be performed with ultrasonic guide (step S103). If the treatment is not to be performed with ultrasonic guide (No at step S103), the radiation treatment apparatus 20 places the subject P on a couch and executes positioning of the subject P (step S104). For example, the radiation treatment apparatus 20 captures a CT image when the CT apparatus is installed in the same room, and compares the CT image with a CT image used in the treatment plan to determine the position of the subject P. Alternatively, the radiation treatment apparatus 20 captures a cone-beam CT image by using a cone-beam CT function, and then registration is performed between a reconstructed image and a CT image used in the treatment plan by using, for example, a bone or an organ as a landmark, thereby determining the position of the subject P. Alternatively, the radiation treatment apparatus 20 captures X-ray images in two directions, and performs registration between the images and a CT image used in the treatment plan on the basis of a characteristic structure to determine the position of the subject P. Then, the radiation treatment apparatus 20 performs radiation treatment on the subject P for which positioning is executed by one of the above-described methods (step S107).

If the treatment is to be performed with ultrasonic guide (Yes at step S103), the treatment plan apparatus 40 supports disposition of the ultrasonic probe 310 onto the subject P by the operator in parallel to the above-described positioning of the subject P (step S105). Subsequently, the treatment plan apparatus 40 determines whether the disposition of the ultrasonic probe 310 is completed (step S106). If it is determined that the disposition of the ultrasonic probe 310 is completed (Yes at step S106), the radiation treatment apparatus 20 performs radiation treatment (step S107). If it is determined that the disposition of the ultrasonic probe 310 is not completed (No at step S106), the treatment plan apparatus 40 again supports disposition of the ultrasonic probe onto the subject P by the operator.

Figure 9:
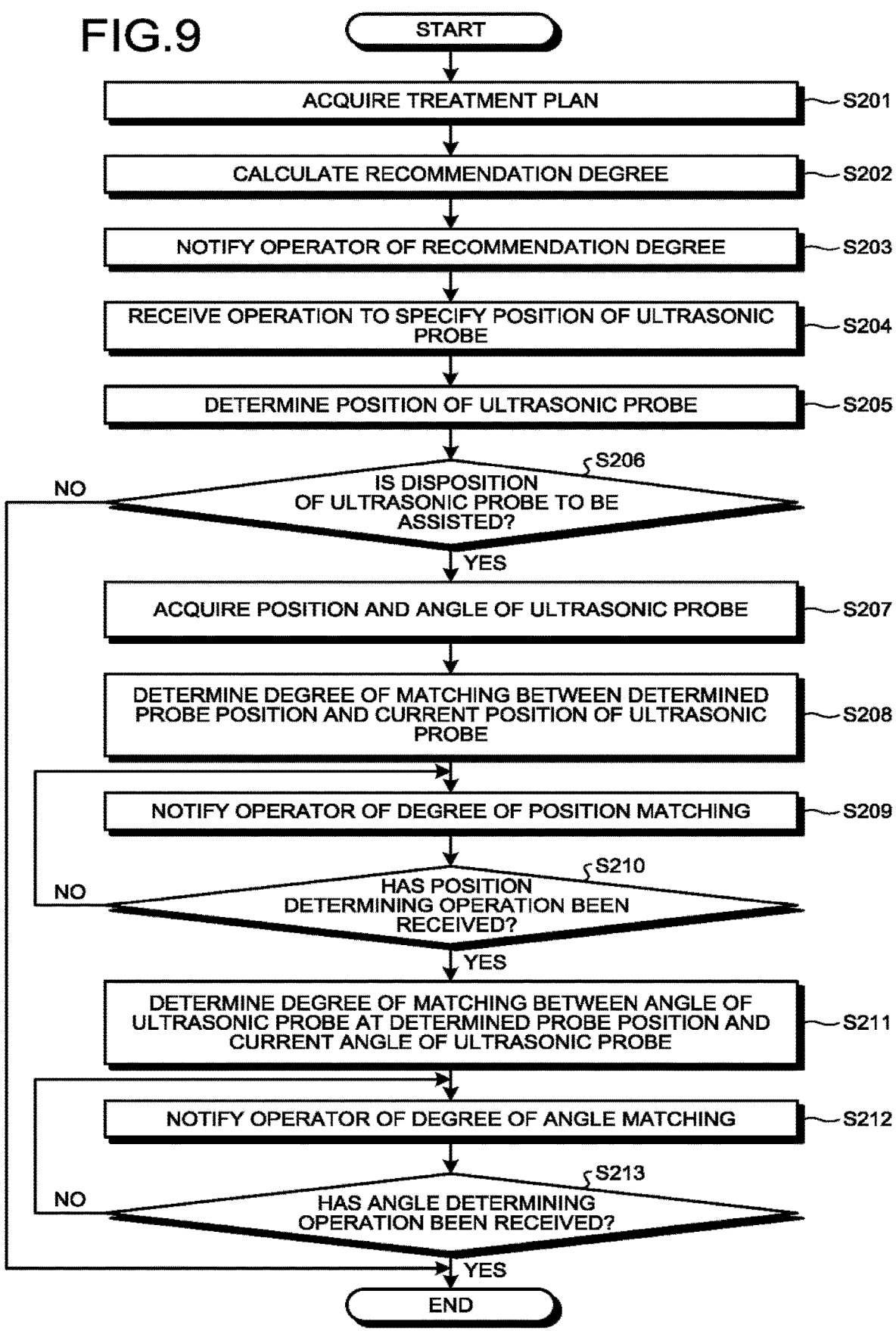
FIG. 9 is a flowchart illustrating an exemplary procedure of processing performed by the treatment plan apparatus according to the first embodiment.

In this manner, in the radiation treatment system 1 according to the first embodiment, the treatment plan apparatus 40 supports disposition of the ultrasonic probe 310 onto the subject P by the operator at step S105 in FIG. 8, thereby achieving efficient execution of ultrasonic guide in radiation treatment. The following describes exemplary processing performed by the treatment plan apparatus 40 according to the first embodiment with reference to FIG. 9. FIG. 9 is a flowchart illustrating an exemplary procedure of the processing performed by the treatment plan apparatus 40 according to the first embodiment. The processing illustrated in FIG. 9 corresponds to the processing at step S105 in FIG. 8.

Steps S201 and S202 illustrated in FIG. 9 are executed by the processing circuitry 440 reading the computer program corresponding to the calculation function 441 from the storage circuitry 430. Steps S203, S209, and S212 illustrated in FIG. 9 are executed by the processing circuitry 440 reading the computer program corresponding to the notification control function 442 from the storage circuitry 430. Step S204 illustrated in FIG. 9 is executed by the processing circuitry 440 reading the computer program corresponding to the reception function 443 from the storage circuitry 430. Step S205 illustrated in FIG. 9 is executed by the processing circuitry 440 reading the computer program corresponding to the determination function 444 from the storage circuitry 430. Step S207 illustrated in FIG. 9 is executed by the processing circuitry 440 reading the computer program corresponding to the acquisition function 445 from the storage circuitry 430. Steps S206, S208, S210, S211, and S213 illustrated in FIG. 9 are executed by the processing circuitry 440 reading the computer program corresponding to the determination function 446 from the storage circuitry 430.

As illustrated in FIG. 9, in the treatment plan apparatus 40, first, the calculation function 441 acquires an irradiation plan (treatment plan) with radiation onto a treatment target site in the subject P (step S201). Subsequently, the calculation function 441 calculates the recommendation degree of disposition of the ultrasonic probe 310 from the treatment plan for each position in the subject P (step S202). For example, the calculation function 441 calculates, from the treatment plan, a value "B" on the basis of the irradiation range of radiation with which the treatment target site is to be irradiated, a value "A" on the basis of distribution of the ultrasonic medium between the ultrasonic probe 310 and the treatment target site, a value "D" on the basis of the distance between the ultrasonic probe 310 and the treatment target site, a value "I" on the basis of the angle between the ultrasonic probe 310 scanning the treatment target site and the contact surface, and a value "S" on the basis of the degree of deformation of the contact surface of the subject P in contact with the ultrasonic probe 310, and calculates an recommendation degree "R" through Expression (1) below by using these numerical values on the basis of the treatment plan:

$$R = aB + bA + cD + dI + eS \qquad (1).$$

In Expression (1), "a", "b", "c", "d", and "e" are predetermined coefficients of "B", "A", "D", "I", and "S", respectively. In Expression (1), "B", "A", "D", "I", and "S" are each a function having, as variables, the coordinates of a position in the subject P. Then, the calculation function 441 calculates the recommendation degree "R" at each position in the subject P from the values "B", "A", "D", "I", and "S" at the position in the subject P.

The following describes an example in which the calculation function 441 calculates the recommendation degree "R" as a numerical value equal to or larger than "0" for each position in the subject P. The following also describes an example in which the calculation function 441 calculates the recommendation degree "R" such that the ultrasonic probe 310 is at a more preferable position as the recommendation degree "R" has a smaller value. The following description will be made on each of "B", "A", "D", "I", and "S" used by the calculation function 441 to calculate the recommendation degree "R".

The description will be first made of the value "B" on the basis of the irradiation range of radiation with which the treatment target site is irradiated. The calculation function 441 first determines whether each position in the subject P is included in the irradiation range of radiation on the basis of a treatment plan. The treatment plan includes information on the position of a treatment target site specified by using CT image data and information on the irradiation angle of radiation emitted by the radiation treatment apparatus 20, which allows the calculation function 441 to determine whether each position in the subject P is included in the irradiation range of radiation.

Subsequently, the calculation function 441 calculates the value "B" at each position in the subject P so that the value "B" at a position not included in the irradiation range is smaller than the value "B" at a position included in the irradiation range. Then, the calculation function 441 calculates, through Expression (1), the recommendation degree "R" indicating that each position in the subject except for any position included in the irradiation range is more recommended than the position included in the irradiation range of radiation.

Specifically, the calculation function 441 calculates the value "B" so that the recommendation degree "R" has a larger value at a position included in the irradiation range among positions in the subject P. For example, the calculation function 441 sets a large value (for example, infinity) to the value "B" at a position included in the irradiation range. When the value "B" has a large value, the recommendation degree "R" has a large value through Expression (1). In this manner, the calculation function 441 can calculate, for each position included in the irradiation range, the recommendation degree "R" indicating that the position is not recommended as a probe position.

The calculation function 441 also calculates the intensity of scatter at any position not included in the irradiation range on the basis of an irradiation condition of radiation, and calculates "B" in accordance with the calculated total intensity of scatter. Then, the calculation function 441 calculates, through Expression (1), the recommendation degree "R" indicating that a position at which the total intensity of scatter is smaller is recommended as a probe position. The calculation function 441 may calculate the total intensity of scatter from a radiation intensity of the first order scattering or from radiation intensities of the first order scattering and the second or higher order scattering.

The calculation function 441 may take into account the fixer of the ultrasonic probe 310 in the calculation of the value "B". For example, the calculation function 441 first acquires, on the basis of the treatment plan, information on the fixer used to fix the ultrasonic probe 310. The calculation function 441 acquires, as the information on the fixer, information such as the size and shape of the fixer and the movable range of any joint of the arm. In the treatment plan, the fixer may be selected for each treatment target site.

Subsequently, the calculation function 441 determines, on the basis of the acquired information on the fixer, whether the ultrasonic probe 310 and the fixer are included in the irradiation range when the ultrasonic probe 310 is disposed at each position in the subject P. Then, the calculation function 441 calculates the value "B" so that the recommendation degree "R" has a larger value at a position at which at least one of the ultrasonic probe 310 and the fixer is included in the irradiation range among positions in the subject P.

For example, the calculation function 441 sets a large value (for example, infinity) to the value "B" at a position at which at least one of the ultrasonic probe 310 and the fixer is included in the irradiation range. When the value "B" has a large value, the recommendation degree "R" has a large value through Expression (1). In this manner, the calculation function 441 can calculate the recommendation degree "R" indicating that any position in the subject P except for a position at which at least one of the ultrasonic probe 310 and the fixer is included in the irradiation range is more recommended than a position at which the ultrasonic probe 310 and the fixer are included in the irradiation range.

The following describes the value "A" on the basis of distribution of the ultrasonic medium between the ultrasonic probe 310 and the treatment target site. For example, the calculation function 441 can acquire distribution of the ultrasonic medium between the ultrasonic probe 310 and the treatment target site from the CT image data generated by the radiation treatment plan CT apparatus 100 and included in the treatment plan. In the following, a region between a position in the subject P and the treatment target site is also referred to as an ultrasonic path. The ultrasonic path is a region determined for each position in the subject P.

For example, the calculation function 441 first determines whether bones and gas are distributed as an ultrasonic medium on the ultrasonic path for each position in the subject P. Subsequently, the calculation function 441 calculates the value "A" at each position in the subject P so that the value "A" at a position at which bones and gas are not distributed on the ultrasonic path is smaller than the value "A" at a position at which bones and gas are distributed. In this case, the calculation function 441 calculates, through Expression (1), the recommendation degree "R" indicating that a position in the subject except for any position at which bones and gas are distributed as ultrasonic media is more recommended as a probe position than a position at which bones and gas are distributed as media. The gas as an ultrasonic medium includes air in a lung of the subject P and gas inside the digestive system.

Specifically, the calculation function 441 calculates the value "A" so that the recommendation degree "R" has a larger value at a position at which bones and gas are distributed on the ultrasonic path among positions in the subject P. For example, the calculation function 441 sets a large value (for example, infinity) to the value "A" at a position at which bones and gas are distributed as ultrasonic media on the ultrasonic path. Then, the calculation function 441 calculates, through Expression (1), for any position at which bones and gas are distributed on the ultrasonic path, the recommendation degree "R" indicating that the position is not recommended as a probe position.

The calculation function 441 evaluates, for any position at which bones and gas are not distributed on the ultrasonic path, non-uniformity of any body tissue on the ultrasonic path and sets a larger value to the value "A" at a more non-uniform position. For example, the calculation function 441 first acquires, from the treatment plan, the CT image data including any body tissue on the ultrasonic path. Subsequently, the calculation function 441 calculates a dispersion value for a pixel value at each position corresponding to the ultrasonic path in the CT image data. Then, the calculation function 441 sets a larger value indicating the body tissue is non-uniform, to the value "A" for a larger dispersion value.

The calculation function 441 may calculate a dispersion value for a CT value acquired by the radiation treatment plan CT apparatus 100, or may calculate a dispersion value for the CT value and an acoustic impedance calculated on the basis of the concept of mutual information. In the latter case, the acoustic impedance can be accurately determined by specifying a material on the basis of dual energy CT. The calculation function 441 may calculate a dispersion value not only from image data by the radiation treatment plan CT apparatus 100, but also from various kinds of medical image data including a body tissue on the ultrasonic path.

The calculation function 441 may evaluate distribution of ultrasonic media on the ultrasonic path by using a plurality of pieces of the CT image data acquired sequentially in time. When the treatment target site is positioned, for example, near a lung and thus moves during radiation treatment, the radiation treatment plan CT apparatus 100 acquires sequentially in time a plurality of pieces of the CT image data including the treatment target site. Then, the calculation function 441 calculates information on motion of the treatment target site on the basis of the pieces of the CT image data. The information on motion includes, for example, the coordinates of a position on the body surface of the subject P, at which the ultrasonic probe 310 is placed, and the coordinates of the position of the treatment target site when each of the pieces of the CT image data is acquired.

For example, the calculation function 441 calculates a plurality of ultrasonic paths each indicating a region between the position of the treatment target site when the corresponding one of the pieces of the CT image data is acquired and the position of a moving body surface of the subject P. In other words, the calculation function 441 calculates the ultrasonic path for each piece of the CT image data for each position in the subject P. Subsequently, the calculation function 441 determines whether bones or gas is distributed on any of the ultrasonic paths for each position in the subject P. If bones or gas is distributed on any of the ultrasonic paths, the calculation function 441 sets a large value (for example, infinity) to the value "A". Alternatively, the calculation function 441 calculates a dispersion value for each of the ultrasonic paths and averages a plurality of dispersion value calculated for the respective ultrasonic paths. Then, the calculation function 441 sets a larger value to the value "A", indicating that a body tissue is non-uniform for a larger average of the dispersion values.

For example, the calculation function 441 calculates a value "A'" on the basis of distribution of the ultrasonic medium between the ultrasonic probe 310 and the treatment target site for each position of the subject P for each of the pieces of the CT image data. Subsequently, the calculation function 441 calculates, for each position of the subject P, an average of a plurality of values "A'" calculated for the respective pieces of the CT image data. Then, the calculation function 441 calculates the recommendation degree "R" by substituting the average calculated for each position in the subject P into "A" in Expression (1).

The following describes the value "D" based on the distance between the ultrasonic probe 310 and the treatment target site. For example, the calculation function 441 first acquires, from the CT image data generated by the radiation treatment plan CT apparatus 100, the distance (length of the ultrasonic path) between the treatment target site and each position in the subject P. Then, the calculation function 441 sets a larger value to the value "D" for a longer ultrasonic path for each position in the subject P. Specifically, the calculation function 441 calculates the value "D" as a function of the distance between the ultrasonic probe 310 and the treatment target site.

The calculation function 441 may define a function that calculates the value "D", by using the attenuation rate of ultrasonic waves on an ultrasonic path. For example, the calculation function 441 may define the function that calculates the value "D" to be a function including the product of the length of the ultrasonic path and the logarithmic attenuation rate of material on the ultrasonic path. Alternatively, for example, the calculation function 441 may define the function that calculates the value "D" to be a function including the product of the length of the ultrasonic path and the reciprocal of the attenuation ratio of material on the ultrasonic path. Specifically, the calculation function 441 defines such a function that the value "D" is likely to be larger as ultrasonic waves are more likely to attenuate due to the physical property of an ultrasonic medium on the ultrasonic path. Then, the calculation function 441 calculates the degree of attenuation of ultrasonic waves transmitted from the ultrasonic probe 310, at the treatment body site, thereby calculating the value "D". The calculation function 441 can calculate the value "D", assuming a soft tissue as a tissue between the ultrasonic probe 310 and the treatment target site.

The calculation function 441 may change the function that calculates the value "D", in accordance with a scanning condition of scanning by the ultrasonic probe 310. For example, the calculation function 441 may define the function that calculates the value "D" to be a function including the product of the length of the ultrasonic path and the frequency of ultrasonic waves. Specifically, the calculation function 441 defines such a function that the value "D" is likely to be larger for a scanning condition under which ultrasonic waves are likely to attenuate because ultrasonic waves are more likely to attenuate at a larger frequency over the same distance. Then, the calculation function 441 calculates the value "D" to be a larger value for a larger frequency of ultrasonic waves. The calculation function 441 can acquire a scanning condition from the transmission and reception circuitry 341 that adjusts, for example, a transmission frequency and a transmission drive voltage. Although the value "D" is defined to be the length of the ultrasonic path or the product of the length of the ultrasonic path and the frequency of ultrasonic waves, the value "D" may be calculated on the basis of the frequency of ultrasonic waves and an attenuation rate to the treatment target site, which is calculated on the basis of the acoustic impedance. Specifically, for example, when the attenuation rate is "80%", the value "D" is calculated to be the reciprocal of a difference obtained by subtracting "0.8" from "1".

The following describes the value "I" on the basis of the angle between the ultrasonic probe 310 scanning the treatment target site and the contact surface. The following describes an example in which a contact surface with the ultrasonic probe 310 is the body surface (skin) of the subject P, but the embodiment is not limited thereto. For example, the contact surface with the ultrasonic probe 310 may be a body surface tissue such as a mucous membrane other than a skin. In a case in which the subject P swallows the ultrasonic probe 310 to perform scanning from the inside (for example, the esophagus) of the subject P, the contact surface is not limited to the body surface.

For example, the calculation function 441 first acquires information on the position of the treatment target site from the treatment plan, and acquires a direction from each position in the subject P to the treatment target site. The direction from each position in the subject P to the treatment target site is aligned with the direction of the ultrasonic probe 310 scanning the treatment target site because scanning is performed while the ultrasonic probe 310 disposed on the subject P is being pointed to the treatment target site.

The calculation function 441 acquires the direction of the contact surface at each position in the subject P from the CT image data acquired by the radiation treatment plan CT apparatus 100. For example, the calculation function 441 acquires, as the direction of the contact surface, the direction of a plane having a normal vector along a perpendicular line toward the skin at each position in the subject P. Then, the calculation function 441 calculates, for each position in the subject P, an angle (hereinafter also simply referred to as a contact angle) between the direction of the ultrasonic probe 310 scanning the treatment target site and the direction of the contact surface.

For example, it is easy to place the ultrasonic probe 310 at a position at which the contact angle is "90°" because the ultrasonic probe 310 only needs to be placed vertical to the skin. Thus, the calculation function 441 calculates "I" to be smaller for a position at which the contact angle is closer to "90°". For example, when disposed at a position at which the contact angle is close to "0°", the ultrasonic probe 310 is tilted with respect to the skin. When the ultrasonic probe 310 is largely tilted, the placement is difficult, and a gap is potentially generated between the ultrasonic probe 310 and the skin. The gap generated between the ultrasonic probe 310 and the skin makes it difficult to acquire ultrasonic images. Thus, the calculation function 441 calculates "I" to be larger for a position at which the contact angle is closer to "0°".

For example, the calculation function 441 sets "I" to be the square of cosine "cos θ" when "θ" represents the contact angle. In this case, "I" is "0" when the contact angle is "90°", and "I" is "1" when the contact angle is "0°". Alternatively, the calculation function 441 calculates the contact angle "θ" in a range from "0°" to "90°", and sets "I" to be cosine "cos θ".

The calculation function 441 calculates the direction of the ultrasonic probe 310 scanning the treatment target site to be a direction to the treatment target site from the central coordinates of a surface of the ultrasonic probe 310 scanning the treatment target site and brought in contact with the skin of the subject P. Then, the calculation function 441 calculates the contact angle from the direction of the ultrasonic probe 310 scanning the treatment target site and the direction of the contact surface, and calculates "I" on the basis of the contact angle.

The following describes the value "S" on the basis of the degree of deformation of the contact surface of the subject P in contact with the ultrasonic probe 310. The degree of deformation indicates ease of deformation of the skin of the subject P, which is in contact with the ultrasonic probe 310. For example, the calculation function 441 calculates the degree of deformation at each position in the subject P on the basis of a nearby tissue or a distance to bone. For example, the calculation function 441 calculates, for each position in the subject P, a distance to a nearest bone from the CT image data acquired by the radiation treatment plan CT apparatus 100. Then, the calculation function 441 calculates the degree of deformation at each position in the subject P so that the degree of deformation is smaller for a shorter distance to the bone.

Then, the calculation function 441 calculates the value "S" to be larger for a smaller degree of deformation for each position in the subject P. For example, when the ultrasonic probe 310 is disposed at a position at which the degree of deformation is large, it is easy to point, to the treatment target site, the ultrasonic probe 310 while being in contact with the skin of the subject P. Thus, the calculation function 441 calculates the value "S" to be small for a position at which the degree of deformation is large. When the ultrasonic probe 310 is disposed at a position at which the degree of deformation is small, and is tilted with respect to the contact surface to cause the ultrasonic probe 310 to point to the treatment target site, a gap is potentially generated between the ultrasonic probe 310 and the skin in some cases. Thus, the calculation function 441 calculates the value "S" to be large for a position at which the degree of deformation is small.

As described above, the calculation function 441 calculates, from the treatment plan, the value "B" on the basis of the irradiation range of radiation with which the treatment target site is irradiated, the value "A" on the basis of distribution of the ultrasonic medium between the ultrasonic probe 310 and the treatment target site, the value "D" on the basis of the distance between the ultrasonic probe 310 and the treatment target site, the value "I" on the basis of the angle between the ultrasonic probe 310 scanning the treatment target site and the contact surface, the value "S" on the basis of the degree of deformation of the contact surface of the subject P in contact with the ultrasonic probe 310. The calculation function 441 calculates the recommendation degree "R" through Expression (1) by using the calculated values "B", "A", "D", "I", and "S".

Figure 10:
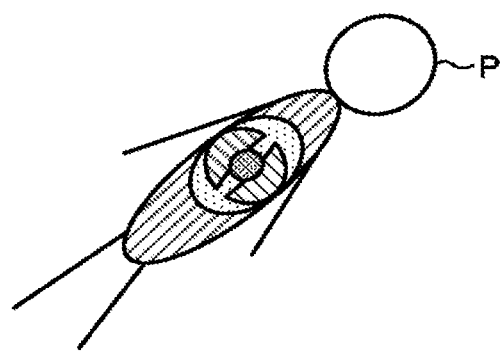
FIG. 10 is a diagram for describing a notification of recommendation degree according to the first embodiment.

Then, the notification control function 442 notifies the operator of the recommendation degree "R" calculated by the calculation function 441 for each position in the subject P, in association with a position in the subject P (step S203). The following describes the notification of the recommendation degree with reference to FIG. 10. FIG. 10 is a diagram for describing the notification of the recommendation degree according to the first embodiment. For example, as illustrated in FIG. 10, the notification control function 442 notifies the operator of the recommendation degree "R" by causing a display (for example, the display 420, the display 220, or the display 330) to display an image provided with a color corresponding to the recommendation degree "R" on a model representing the subject P. The notification control function 442 may use, as the color corresponding to the recommendation degree "R", one of hue, saturation, and luminance (e.g. signal intensity), or a combination of two or more of hue, saturation, and luminance.

The notification control function 442 can generate the model representing the subject P on the basis of model data stored in, for example, the storage circuitry 430 in advance. The model data is an image obtained from, through a medical image examination apparatus such as CT, a human body having a typical body shape in accordance with a plurality of combinations of body related parameters such as age, adult/child, male/female, weight, and height.

For example, the notification control function 442 first reads, from the storage circuitry 430, corresponding model data in accordance with subject information read from a treatment plan or the PACS server 60. Subsequently, the notification control function 442 extracts an anatomical feature point in the CT image data (volume data) of the subject P received from the radiation treatment plan CT apparatus 100. The notification control function 442 compares the anatomical feature point in the CT image data and a feature point in the read model data, and associates the coordinate space of the volume data and the coordinate space of the model data with each other. In this manner, the notification control function 442 acquires model data approximated to the CT image data through the feature-point association.

Specifically, the notification control function 442 can generate a human body model in accordance with the body shape of the subject P from model data stored in the storage circuitry 430. Then, the notification control function 442 can display the recommendation degree "R" calculated for each position in the subject P at each position on the generated human body model with one of hue, saturation, and luminance, or a combination of two or more of hue, saturation, and luminance. The notification control function 442 may use, in place of the above-described human body model, the CT image data of the subject P acquired by, for example, the radiation treatment plan CT apparatus 100.

The notification control function 442 may display a multi planar reconstruction (MPR) image as well as notify the operator of the recommendation degree "R" in association with a position in the subject P. The notification control function 442 can generate the MPR image from model data, CT image data transmitted from the radiation treatment plan CT apparatus 100, or any other CT apparatus.

For example, the notification control function 442 displays an MPR image having three mutually orthogonal planes and including a position at which the recommendation degree "R" is calculated to be the smallest and a position specified by the operator through the input circuitry 410 among positions in the subject P. The notification control function 442 can cause the treatment target site to be included in at least two planes of the three planes of the displayed MPR image. For example, the notification control function 442 displays an MPR image having three mutually orthogonal planes and including the treatment target site. The notification control function 442 can cause a position at which the recommendation degree "R" is calculated to be the smallest or a position specified by the operator through the input circuitry 410 to be included in at least two planes of the three planes of the displayed MPR image.

In the above-described example, the calculation function 441 calculates the single recommendation degree "R" by using "B", "A", "D", "I", and "S". However, the calculation function 441 may calculate a plurality of recommendation degrees. For example, the calculation function 441 calculates a first recommendation degree through Expression (2) below by using the four values of the value "B" on the basis of the irradiation range of radiation with which the treatment target site is irradiated, the value "A" on the basis of distribution of the ultrasonic medium between the ultrasonic probe 310 and the treatment target site, the value "D" on the basis of the distance between the ultrasonic probe 310 and the treatment target site, and the value "S" on the basis of the degree of deformation of the contact surface of the subject P in contact with the ultrasonic probe 310. In Expression (2), "a", "b", "c", and "e" are the same as those in Expression (1):

$$R=aB+bA+cD+eS \quad (2).$$

In addition, the calculation function 441 calculates a second recommendation degree by multiplying, with a predetermined coefficient "d", the value "I" on the basis of the angle between the ultrasonic probe 310 scanning the treatment target site and the contact surface. Then, the notification control function 442 notifies the operator of each recommendation degree in association with a position in the subject P. For example, the notification control function 442 display an image of the human body model, in which the first recommendation degree is expressed in one of hue and saturation or a combination of hue and saturation and the second recommendation degree is expressed in luminance. The notification control function 442 notifies the operator of the recommendation degree at each position in the subject P by causing a display (for example, the display 420, the display 220, or the display 330) to display the image of the human body model.

Alternatively, the notification control function 442 may generate, for each recommendation degree calculated by the calculation function 441, an image illustrating the recommendation degree at each position in the subject P, and perform switching of the recommendation degree, notification of which is given, in response to an operation from the operator. The values "B", "A", "D", "I", and "S" in the recommendation degree calculation may be used in an optional combination, and may be used in a duplicate manner when a plurality of recommendation degrees are calculated.

Subsequently, the reception function 443 receives, from the operator through the input circuitry 410, a specifying operation to specify the position of the ultrasonic probe 310 in the subject P (step S204). Specifically, the reception function 443 receives, from the operator referring to the recommendation degree displayed by the notification control function 442 in association with a position in the subject P, a specifying operation to specify a position determined to be appropriate as the position of the ultrasonic probe 310.

Figure 11A:
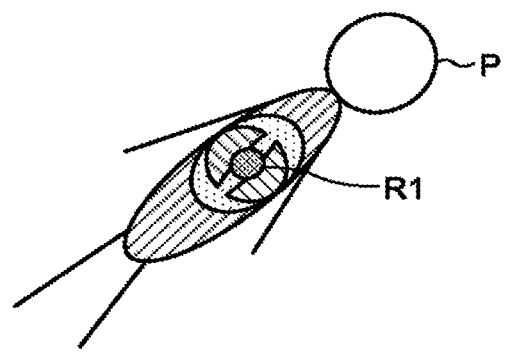
FIG. 11A is a diagram for describing an operation to specify the position of an ultrasonic probe according to the first embodiment.
Figure 11B:
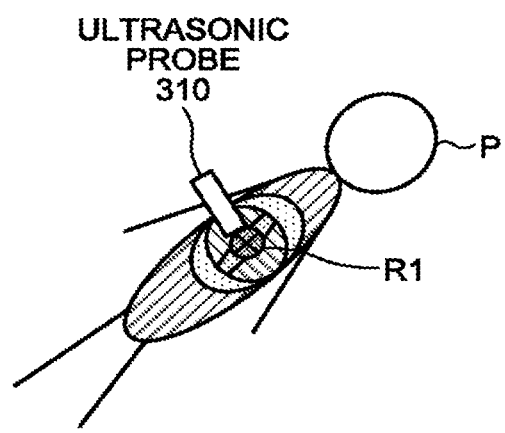
FIG. 11B is a diagram for describing the operation to specify the position of the ultrasonic probe according to the first embodiment.

The following describes an exemplary operation to specify the position of the ultrasonic probe 310 with reference to FIGS. 11A and 11B. FIGS. 11A and 11B are diagrams for describing the operation to specify the position of the ultrasonic probe 310 according to the first embodiment. First, as illustrated in FIG. 11A, the notification control function 442 displays the recommendation degree calculated for each position in the subject P in a corresponding hue at the corresponding position on the human body model. Subsequently, the operator determines the position of the ultrasonic probe 310. For example, the operator determines the position of the ultrasonic probe 310 to be a position R1 at which the recommendation degree is the smallest among positions on the human body model in which the recommendation degree is expressed in hue. Then, the reception function 443 receives a specifying operation to specify the position R1 through an operation on the mouse included in the input circuitry 410.

The notification control function 442 may give notification of an angle of, with respect to the contact surface, the ultrasonic probe 310 scanning the treatment target site at a position for which the specifying operation is received. For example, as illustrated in FIG. 11B, the notification control function 442 may display, at the position R1 for which the specifying operation is received, a figure representing the ultrasonic probe 310 pointing to the treatment target site. Then, if the operator determines that the angle of the ultrasonic probe 310 being displayed is inappropriate, the reception function 443 may receive again the specifying operation to specify the position of the ultrasonic probe 310 in the subject P.

Then, the determination function 444 determines the position of the ultrasonic probe 310 in the subject P (step S205). For example, the determination function 444 determines a probe position to be a position for which the reception function 443 has received the specifying operation from the operator at step S204. Step S204 does not need to be performed as appropriate. In this case, the determination function 444 determines the probe position in accordance with the recommendation degree calculated by the calculation function 441. For example, the determination function 444 determines the probe position to be the position at which the recommendation degree is the smallest.

As described above, the processing circuitry 440 according to the embodiment supports determination of the position of the ultrasonic probe 310 through calculation of the recommendation degree for each position of the subject P.

The radiation treatment apparatus 20 may place the subject P on the couch and execute positioning of the subject P in parallel to steps S201 to S205 executed by the processing circuitry 440. The positioning of the subject P by the radiation treatment apparatus 20 is the same as the positioning at step S104 in FIG. 8.

Subsequently, the determination function 446 determines whether to assist the disposition of the ultrasonic probe 310 (step S206). For example, the determination function 446 displays buttons indicating "Yes" and "No" in a GUI dialogue box displayed on the display 420, and determines whether to assist the disposition of the ultrasonic probe 310 depending on a press on a button by the operator. Alternatively, for example, the determination function 446 determines whether to assist the disposition depending on whether a GUI check box displayed on the display 420 is checked. If the disposition of the ultrasonic probe 310 is not to be assisted (No at step S206), processing for supporting the disposition of the ultrasonic probe 310 is ended.

If the disposition of the ultrasonic probe 310 is assisted (Yes at step S206), the acquisition function 445 acquires the position and angle of the ultrasonic probe 310 (step S207). The ultrasonic probe 310 includes the sensor 350 for specifying a position and an angle in the three-dimensional coordinate system. The acquisition function 445 acquires the position and angle of the ultrasonic probe 310 through reception of position information and angle information detected by the sensor 350. Specifically, the position and angle of the ultrasonic probe 310 acquired by the acquisition function 445 indicate the current position and angle of the ultrasonic probe 310.

Subsequently, the determination function 446 determines the degree of matching between the probe position determined by the determination function 444 and the position of the ultrasonic probe 310 acquired by the acquisition function 445 (step S208). Hereinafter, the position of the ultrasonic probe 310 in the subject P determined by the determination function 444 is also referred to as a recommended position. The position of the ultrasonic probe 310 in the subject P acquired by the acquisition function 445 is also referred to as a current position.

In the radiation treatment system 1, registration is performed in advance between the coordinate system of the radiation treatment plan CT apparatus 100, the coordinate system of the radiation treatment apparatus 20, and the coordinate system of the ultrasonic diagnostic apparatus 30. Thus, the determination function 446 can uniquely determine, for example, a positional relation between the recommended position determined by the determination function 444 in the coordinate system of the radiation treatment plan CT apparatus 100 and the current position acquired by the acquisition function 445 in the coordinate system of the ultrasonic diagnostic apparatus 30. Then, the determination function 446 calculates, for example, the distance between the coordinates of the recommended position and the coordinates of the current position, and determines the degree of matching (hereinafter also referred to as the degree of position matching) between the recommended position and the current position to be inversely proportional to the calculated distance.

Subsequently, the notification control function 442 notifies the operator of the degree of position matching determined by the determination function 446 (step S209). For example, the notification control function 442 notifies the operator of the degree of matching by displaying a color or number corresponding to the degree of position matching on, for example, the display 420, the display 220, or the display 330, or emitting sound corresponding to the degree of matching or other sound. Specifically, the notification control function 442 notifies the operator of the degree of matching determined by the determination function 446 in hue, saturation, luminance, number, sound, or a combination of two or more of hue, saturation, luminance, number, and sound.

The determination function 446 determines whether a determining operation to determine a position at which the ultrasonic probe 310 is placed has been received from the operator (step S210). If the disposition of the ultrasonic probe 310 at the recommended position is not completed, the determination function 446 has received no position determining operation (No at step S210), and the notification control function 442 notifies the operator of the degree of position matching again.

If the operator determines that the disposition of the ultrasonic probe 310 at the recommended position is completed, the determination function 446 receives the position determining operation (Yes at step S210). Subsequently, the determination function 446 determines the degree of matching between the angle between the ultrasonic probe 310 scanning the treatment target site at the probe position (recommended position) determined by the determination function 444 and the contact surface of the subject P in contact with the ultrasonic probe 310, and the angle of the ultrasonic probe 310 acquired by the acquisition function 445 (step S211).

The ultrasonic probe 310 scanning the treatment target site at the recommended position is pointing to a direction from the recommended position toward the treatment target site. The contact surface of the subject P in contact with the ultrasonic probe 310 is, for example, a surface having a normal vector along a perpendicular line from the skin of the subject P at the recommended position. In the following, the angle between the ultrasonic probe 310 scanning the treatment target site at the recommended position and the contact surface of the subject P in contact with the ultrasonic probe 310 is also referred to as a recommended angle.

The angle of the ultrasonic probe 310 acquired by the acquisition function 445 is, for example, an angle between a direction to which the ultrasonic probe 310 is currently pointing and the contact surface of the subject P at the recommended position. In the following, the angle of the ultrasonic probe 310 acquired by the acquisition function 445 is also referred to as the current angle. Then, the determination function 446 can uniquely determine a relation between the recommended angle and the current angle because registration is performed among the coordinate system of each apparatus in the radiation treatment system 1 in advance. Then, the determination function 446 calculates, for example, a difference between the recommended angle and the current angle, and determines the degree of matching (hereinafter also referred to as the degree of angle matching) between the recommended angle and the current angle to be inversely proportional to the calculated difference.

Subsequently, the notification control function 442 notifies the operator of the degree of angle matching determined by the determination function 446 (step S212). For example, the notification control function 442 notifies the operator of the degree of angle matching by causing, for example, the display 420, the display 220, or the display 330 to display a color or number corresponding to the degree of angle matching, or emitting a sound corresponding to the degree of angle matching or other sound. Specifically, the notification control function 442 notifies the operator of the degree of angle matching determined by the determination function 446 in one of hue, saturation, luminance, number, and sound, or a combination of two or more of hue, saturation, luminance, number, and sound.

The determination function 446 determines whether a determining operation to determine an angle at which the ultrasonic probe 310 is placed has been received from the operator (step S213). If an operation to match the angle of the ultrasonic probe 310 with the recommended angle is not completed, the determination function 446 has received no angle determining operation (No at step S213), and the notification control function 442 notifies the operator of the degree of angle matching again. If the operation to match the angle of the ultrasonic probe 310 with the recommended angle is completed, the determination function 446 has received the angle determining operation from the operator (Yes at step S213), and processing for supporting the disposition of the ultrasonic probe 310 is ended.

The notification control function 442 may simultaneously give notification of the degree of matching of the position of the ultrasonic probe 310 and the degree of angle matching, which are determined by the determination function 446. For example, the notification control function 442 simultaneously gives notification of the degree of position matching and the degree of angle matching by presenting, to the operator, an image obtained by synthesizing, on the human body model, a figure representing the ultrasonic probe 310 at the recommended position and the recommended angle and a figure representing the ultrasonic probe 310 at the current position and the current angle.

When the disposition of the ultrasonic probe 310 is ended, the ultrasonic diagnostic apparatus 30 generates an ultrasonic image including the treatment target site, and presents the generated ultrasonic image to the operator through, for example, the display 330. When having received a command to start radiation treatment, the radiation treatment apparatus 20 executes radiation treatment by irradiating the subject P with radiation according to the treatment plan while checking the position and motion of the treatment target site with ultrasonic guide.

As described above, according to the first embodiment, the calculation function 441 calculates, for each position in the subject P on the basis of an irradiation plan with radiation on a target site of the subject P, the recommendation degree of disposition of the ultrasonic probe 310 that scans the target site at irradiation with radiation. The notification control function 442 notifies the operator of the recommendation degree in association with a position in the subject P. Accordingly, the treatment plan apparatus 40 according to the first embodiment can support disposition of the ultrasonic probe in radiation treatment.

In addition, according to the first embodiment, the calculation function 441 calculates the recommendation degree on the basis of the value "B" based on the irradiation range of radiation with which the treatment target site is irradiated. Accordingly, the treatment plan apparatus 40 according to the first embodiment can support disposition of the ultrasonic probe 310 on the subject P to avoid reduction in the efficiency of radiation treatment due to attenuation of radiation when transmitting through the ultrasonic probe 310 and the fixer, and degradation of the ultrasonic probe 310.

In addition, according to the first embodiment, the calculation function 441 calculates the value "B" on the basis of the intensity of scatter and calculates the recommendation degree. Accordingly, the treatment plan apparatus 40 according to the first embodiment can reduce degradation of the ultrasonic probe 310 due to scatter when the ultrasonic probe 310 is disposed at a position not included in the irradiation range of radiation.

In addition, according to the first embodiment, the calculation function 441 calculates the recommendation degree on the basis of the value "A" based on distribution of the ultrasonic medium between the ultrasonic probe 310 and the treatment target site. Accordingly, the treatment plan apparatus 40 according to the first embodiment can support disposition of the ultrasonic probe 310 on the subject P to avoid degradation of the quality of an ultrasonic image at the treatment target site due to distribution of bones and gas as ultrasonic media on the ultrasonic path.

In addition, according to the first embodiment, the calculation function 441 calculates a dispersion value on the basis of a signal value at each position on the ultrasonic path, calculates the value "A" on the basis of the calculated dispersion value, and calculates the recommendation degree. Accordingly, when the ultrasonic probe 310 is disposed at a position at which bones and gas are not distributed as ultrasonic media on the ultrasonic path, the treatment plan apparatus 40 according to the first embodiment can support disposition of the ultrasonic probe 310 on the subject P to avoid degradation of the quality of an ultrasonic image caused by attenuation of ultrasonic waves due to non-uniform distribution of body tissues as a sound wave medium on the ultrasonic path.

In addition, according to the first embodiment, the calculation function 441 calculates information on motion of the treatment target site on the basis of a plurality of pieces of the CT image data, calculates temporally changing distribution of an ultrasonic medium on the ultrasonic path, calculates the value "A" on the basis of the calculated distribution, and calculates the recommendation degree. Accordingly, the treatment plan apparatus 40 according to the first embodiment can support disposition of the ultrasonic probe 310 on the subject P when the treatment target site is positioned, for example, near a lung and thus moves during radiation treatment.

In addition, according to the first embodiment, the calculation function 441 calculates the recommendation degree on the basis of the value "D" based on the distance between the ultrasonic probe 310 and the treatment target site. Accordingly, the treatment plan apparatus 40 according to the first embodiment can support disposition of the ultrasonic probe 310 on the subject P to avoid degradation of the quality of an ultrasonic image at the treatment target site due to attenuation of ultrasonic waves arriving at the treatment target site through a long ultrasonic path.

In addition, according to the first embodiment, the calculation function 441 defines the function that calculates the value "D", by using the attenuation rate of ultrasonic waves on an ultrasonic path and a scanning condition, and calculates the recommendation degree. Accordingly, the treatment plan apparatus 40 according to the first embodiment can more appropriately calculate the degree of attenuation of ultrasonic waves arriving at the treatment target site.

In addition, according to the first embodiment, the calculation function 441 calculates the recommendation degree on the basis of the value "I" based on the angle between the ultrasonic probe 310 scanning the treatment target site and the contact surface. Accordingly, the treatment plan apparatus 40 according to the first embodiment can support disposition of the ultrasonic probe 310 on the subject P to avoid difficulty in disposition of the ultrasonic probe 310 being largely tilted with respect to the skin of the subject P.

In addition, according to the first embodiment, the calculation function 441 calculates the recommendation degree on the basis of the value "S" based on the degree of deformation of the contact surface of the subject P in contact with the ultrasonic probe 310. Accordingly, the treatment plan apparatus 40 according to the first embodiment can support disposition of the ultrasonic probe 310 on the subject P to allow the ultrasonic probe 310 to be tilted while being closely attached to the skin of the subject P.

In addition, according to the first embodiment, the determination function 446 determines the degree of matching between the recommended position and the current position of the ultrasonic probe 310, and the degree of matching between the recommended angle and the current angle, and the notification control function 442 notifies the operator of the determined degrees of matching. Accordingly, the treatment plan apparatus 40 according to the first embodiment can assist the disposition of the ultrasonic probe 310 on the subject P.

In addition, according to the first embodiment, the notification control function 442 notifies the operator of the degree of matching between the recommended position and the current position of the ultrasonic probe 310, and the degree of matching between the recommended angle and the current angle. Accordingly, the treatment plan apparatus 40 according to the first embodiment allows easy disposition of the ultrasonic probe 310 by avoiding difficulty in simultaneously adjusting a position and an angle when placing the ultrasonic probe 310 on the subject P.

Although the above description is made on the first embodiment, various kinds of different configurations other than the first embodiment described above may be achieved.

In the first embodiment described above, the operator is notified of a calculated recommendation degree. However, the embodiment is not limited thereto. For example, the calculation function 441 may correct a treatment plan on the basis of a recommendation degree in addition to or in place of the notification of a calculated recommendation degree to the operator.

For example, the calculation function 441 corrects the treatment plan when determining that no position is appropriate as the position of the ultrasonic probe 310, as a result of calculation of the recommendation degree for each position in the subject P. For example, the calculation function 441 compares a minimum value of the recommendation degree calculated for each position in the subject P to a threshold. If the minimum value of the recommendation degree is larger than the threshold, the calculation function 441 determines that no position is appropriate for disposition of the ultrasonic probe 310.

When it is determined no position is appropriate for disposition of the ultrasonic probe 310, the calculation function 441 corrects, for example, the frequency of ultrasonic waves in the treatment plan. When the treatment plan is corrected so that the frequency is reduced, ultrasonic waves are less likely to attenuate, which enables scanning of the treatment target site from a farther position. In other words, when the treatment plan is corrected so that the frequency is reduced, the value "D" based on the distance between the ultrasonic probe 310 and the treatment target site is reduced, and the recommendation degree at each position in the subject P is reduced. For example, the calculation function 441 corrects the frequency so that the minimum value of the recommendation degree at each position in the subject P is lower than a threshold.

Then, the calculation function 441 calculates the recommendation degree again on the basis of the corrected treatment plan, and the notification control function 442 notifies the operator of the recommendation degree based on the corrected treatment plan. There exists a position at which the recommendation degree is lower than the threshold after the frequency correction, and thus the notification control function 442 can present, to the operator, an appropriate position at which the ultrasonic probe 310 is to be disposed.

For example, the calculation function 441 may correct the treatment plan when it is determined that there exists an appropriate position at which the ultrasonic probe 310 is to be disposed. For example, the calculation function 441 compares the minimum value of the recommendation degree calculated for each position in the subject P to the threshold. If the minimum value of the recommendation degree is smaller than the threshold, the calculation function 441 determines that there exists an appropriate position at which the ultrasonic probe 310 is to be disposed.

When it is determined there exists an appropriate position at which the ultrasonic probe 310 is to be disposed, the calculation function 441 corrects the treatment plan so that, for example, the frequency of ultrasonic waves is increased. In this case, the value "D" is increased, and the recommendation degree at each position in the subject P is increased. Thus, the calculation function 441 corrects the treatment plan so that the frequency of ultrasonic waves is increased while there exists an appropriate position at which the ultrasonic probe 310 is to be disposed. Then, the calculation function 441 enables generation of a high-contrast ultrasonic image on the basis of high-frequency ultrasonic waves by correcting the treatment plan. The notification control function 442 presents, to the operator, the appropriate position at which the ultrasonic probe 310 is to be disposed.

In the above-described example, the frequency of ultrasonic waves used for scanning of the treatment target site is corrected in the treatment plan. However, the embodiment is not limited thereto, and the calculation function 441 may correct any other condition (for example, the direction of irradiation with treatment radiation) in the treatment plan.

In the first embodiment, the calculation function 441 calculates the recommendation degree "R" as a numerical value that is equal to or larger than "0" and is smaller when indicating a more preferable position of the ultrasonic probe 310. However, the embodiment is not limited thereto. For example, the calculation function 441 may calculate the recommendation degree "R" as a value that is larger when indicating a more preferable position of the ultrasonic probe 310. The calculation function 441 calculates the recommendation degree "R" as a numerical value in an optional range. For example, the calculation function 441 may evaluate the recommendation degree "R" to be in two or more levels. For example, the calculation function 441 may calculate the recommendation degree "R" indicating whether each position in the subject P is appropriate as the position of the ultrasonic probe 310.

In the first embodiment, the recommended angle and the current angle of the ultrasonic probe 310 are calculated by using the contact surface of the subject P at the recommended position as a reference, but the embodiment is not limited thereto. For example, the determination function 446 may calculate the recommended angle and the current angle of the ultrasonic probe 310 by using, as a reference, an optional surface such as the floor or a wall of a room in which the radiation treatment apparatus 20 is installed. For example, the determination function 446 may calculate the inner product of the directional vector of the ultrasonic probe 310 scanning the treatment target site at the recommended position and the directional vector of the ultrasonic probe 310 acquired by the acquisition function 445, and determine the degree of angle matching to be larger for a larger value of the inner product.

In the first embodiment, the CT image data is used as volume data used to prepare the treatment plan. However, the embodiment is not limited thereto, and volume data acquired by, for example, an MRI apparatus, a PET apparatus, or a SPECT apparatus may be used.

In the first embodiment described above, the treatment plan apparatus 40 that executes each function achieved by the processing circuitry 440 is described as a support apparatus that supports disposition of the ultrasonic probe 310 in radiation treatment. However, the embodiment is not limited thereto, and the above-described support apparatus may be achieved by any apparatus illustrated in FIG. 1 or any apparatus other than the apparatuses illustrated in FIG. 1.

For example, the radiation treatment apparatus 20 may support disposition of the ultrasonic probe 310 in radiation treatment. For example, first, the system control circuitry 260 of the radiation treatment apparatus 20 acquires a treatment plan for a treatment target site in the subject P from the treatment plan apparatus 40. Subsequently, the system control circuitry 260 calculates the recommendation degree of disposition of the ultrasonic probe 310 for each position in the subject P on the basis of the treatment plan, and notifies the operator of the calculated recommendation degree in association with a position in the subject P, thereby supporting disposition of the ultrasonic probe 310 in radiation treatment. Specifically, the above-described support apparatus is achieved in the radiation treatment apparatus 20 by the system control circuitry 260 executing each function achieved by the processing circuitry 440.

In the above description of the radiation treatment plan CT apparatus 100, the radiation treatment apparatus 20, the ultrasonic diagnostic apparatus 30, and the treatment plan apparatus 40, the term "processor" means, for example, a central processing unit (CPU), a graphics processing unit (GPU), or circuitry such as an application specific integrated circuit (ASIC) or a programmable logic device (for example, a simple programmable logic device (SPLD), a complex programmable logic device (CPLD), or a field programmable gate array (FPGA)). A processor achieves a function by reading a computer program stored in storage circuitry and executing the computer program. The computer program may be directly incorporated in circuitry of the processor instead of being stored in the storage circuitry. In this case, the processor achieves a function by reading the computer program incorporated in the circuitry and executing the computer program. Each processor according to the present embodiment may be provided as a single circuit, and alternatively, a plurality of independent circuits may be combined as one processor to achieve a function of the processor.

Each component of each device described in the first embodiment is a functional concept and does not necessarily require a physical configuration as illustrated. In other words, specific modes of separation and integration of each device are not limited to those illustrated, and the entire or part of the device may be functionally or physically separated or integrated in optional units depending on various kinds of loads and use conditions. In addition, the entire or optional part of processing functionality provided in each device may be achieved by a CPU and a computer program analyzed and executed by this CPU, or achieved as wired logic hardware.

The support method described in the first embodiment may be achieved by executing a previously prepared support computer program at a computer such as a personal computer or a work station. This support computer program may be distributed through a network such as the Internet. This support computer program may also be recorded on a computer-readable recording medium such as a hard disk, a flexible disk (FD), a CD-ROM, an MO, or a DVD, and executed through reading out from the recording medium by a computer.

As described above, according to the first and the second embodiments, disposition of an ultrasonic probe in radiation treatment can be supported.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A support apparatus comprising:
processing circuitry configured to:
calculate for each of a plurality of positions in a subject, based on (1) an irradiation plan of a radiation treatment for a target site of the subject and (2) prospective degradation of an ultrasonic probe by radiation used in the radiation treatment, a recommendation degree of disposition of the ultrasonic probe, wherein the ultrasonic probe is configured to scan the target site with ultrasonic waves when the target site is targeted with the radiation, wherein the recommendation degree corresponds to a numerical value; and
cause a display to display information in which the recommendation degree is displayed in association with each of the plurality of positions in the subject, the recommendation degree being indicated in one of hue, saturation, and luminance, or a combination of two or more of hue, saturation, and luminance, at each position of the plurality of positions in the subject, such that multiple positions have associated therewith one of hue, saturation, and luminance, or a combination of two or more of hue, saturation, and luminance.

2. The support apparatus according to claim 1, wherein the processing circuitry is configured to calculate the recommendation degree based on at least one of a spatial irradiation range on where the radiation is irradiated, distribution of an ultrasonic medium between the ultrasonic probe and the target site, a distance between the ultrasonic probe and the target site, a degree of deformation of a contact surface of the subject in contact with the ultrasonic probe, and an angle between the ultrasonic probe when scanning the target site and the contact surface.

3. The support apparatus according to claim 2, wherein the processing circuitry is configured to calculate, for a first position in the subject except for a second position included in the spatial irradiation range, the recommendation degree such that the first position in the subject is more recommended than the second position.

4. The support apparatus according to claim 2, wherein the processing circuitry is configured to calculate, for a first position in the subject except for a second position included in the spatial irradiation range, the recommendation degree further based on an intensity of scatter of the radiation at the first position.

5. The support apparatus according to claim 2, wherein the processing circuitry is configured to calculate, for a first position in the subject except for a second position at which bones or gas is distributed as the ultrasonic medium between the ultrasonic probe and the target site, the recommendation degree such that the first position in the subject is more recommended than the second position at which bones or gas is distributed as the ultrasonic medium.

6. The support apparatus according to claim 2, wherein the processing circuitry is configured to
further acquire a CT image including any body tissue of the subject on an ultrasonic path of the ultrasonic waves transmitted from the ultrasonic probe, and
calculate a dispersion value based on a signal value of the CT image for each of a plurality of positions of the body tissue in a region between the ultrasonic probe and the target site, and calculate the recommendation degree based on the calculated dispersion value.

7. The support apparatus according to claim 2, wherein the processing circuitry is configured to calculate information on motion of the target site based on a plurality of medical images each including the target site and acquired sequentially in time, calculate temporally changing distribution of the ultrasonic medium between the ultrasonic probe and the target site based on the medical images and the information on motion, and calculate the recommendation degree based on the calculated distribution of the ultrasonic medium.

8. The support apparatus according to claim 2, wherein the processing circuitry is configured to calculate a degree of attenuation, at the target site, of the ultrasonic waves transmitted from the ultrasonic probe based on the distance and a scanning condition of scanning by the ultrasonic probe, and calculate the recommendation degree based on the calculated degree of attenuation.

9. The support apparatus according to claim 2, wherein the processing circuitry is configured to calculate the degree of deformation based on a tissue near the contact surface and a distance from the contact surface to a bone.

10. The support apparatus according to claim 2, wherein the processing circuitry is configured to calculate the angle between the ultrasonic probe scanning the target site and the contact surface to be an angle of the contact surface with respect to a direction to the target site from a center of a surface of the ultrasonic probe scanning the target site and brought in contact with the contact surface.

11. The support apparatus according to claim 2, wherein the processing circuitry is configured to calculate, for a first position in the subject except for a second position at which at least one of the ultrasonic probe and a fixer of the ultrasonic probe is included in the spatial irradiation range of radiation, the recommendation degree such that the first position in the subject is more recommended than the second position at which at least one of the ultrasonic probe and the fixer is included in the spatial irradiation range of radiation.

12. The support apparatus according to claim 1, wherein the processing circuitry is configured to:
calculate the recommendation degree as a first recommendation degree based on at least one of a spatial irradiation range on where the radiation is irradiated, distribution of an ultrasonic medium between the ultrasonic probe and the target site, a distance between the ultrasonic probe and the target site, and a degree of deformation of a contact surface of the subject in contact with the ultrasonic probe, and calculate a second recommendation degree based on an angle between the ultrasonic probe scanning the target site and the contact surface, and
cause the display to display information in which the first recommendation degree for each position of the subject is expressed in one of hue and saturation, or a combination of hue and saturation, and the second recommendation degree for each position of the subject is expressed in luminance.

13. The support apparatus according to claim 1, wherein the processing circuitry is configured to:
receive, from an operator, a specifying operation to specify a position of the ultrasonic probe, and
give notification of, at the position specified by the specifying operation, a recommended angle of the ultrasonic probe when scanning the target site with respect to a contact surface of the subject.

14. The support apparatus according to claim 1, wherein the processing circuitry is configured to:
acquire a current position and a current angle of the ultrasonic probe,
determine a planned position of the ultrasonic probe with respect to the subject based on an input operation by an operator or the recommendation degree,
determine a degree of matching between the determined planned position and the current position of the ultrasonic probe,
determine a degree of matching between an angle between the ultrasonic probe when scanning the target site at the determined planned position and a contact surface of the subject in contact with the ultrasonic probe, and the current angle of the ultrasonic probe, and
notify the operator of the determined degrees of matching.

15. The support apparatus according to claim 14, wherein the processing circuitry is configured to give notification of each determined degree of matching in one of hue, saturation, luminance, number, and sound, or a combination of two or more of hue, saturation, luminance, number, and sound.

16. The support apparatus according to claim 14, wherein the processing circuitry is configured to give notification of both of the determined degree of matching between the positions and the determined degree of matching between the angles individually.

17. The support apparatus according to claim 1, wherein the processing circuitry is configured to correct the irradiation plan based on the recommendation degree.

18. The support apparatus according to claim 1, wherein the processing circuitry is configured to calculate the recommendation degree by using Expression (1), where "B" is a value on the basis of an irradiation range on where the radiation is irradiated, "A" is a value on the basis of distribution of an ultrasonic medium between the ultrasonic probe and the target site, "D" is a value on the basis of distance between the ultrasonic probe and the target site, "I" is a value on the basis of an angle between the ultrasonic probe scanning the target site and contact surface, "S" is a value on the basis of a degree of deformation of the contact surface of the subject in contact with the ultrasonic probe, "a", "b", "c", "d", and "e" are respectively predetermined coefficients of "B", "A", "D", and "S":

$$R = aB + bA + cD + dI + eS \tag{1}$$

19. A method comprising:
calculating for each of a plurality of positions in a subject, based on (1) an irradiation plan of a radiation treatment for a target site of the subject and (2) prospective degradation of an ultrasonic probe by radiation used in the radiation treatment, a recommendation degree of disposition of the ultrasonic probe, wherein the ultrasonic probe is configured to scan the target site with ultrasonic waves when the target site is targeted with the radiation, wherein the recommendation degree corresponds to a numerical value; and causing a display to display information in which the recommendation degree is displayed in association with each of the plurality of positions in the subject, the recommendation degree being indicated in one of hue, saturation, and luminance, or a combination of two or more of hue, saturation, and luminance, at each position of the plurality of positions in the subject, such that multiple positions have associated therewith one of hue, saturation, and luminance, or a combination of two or more of hue, saturation, and luminance.

\* \* \* \* \*